(12) United States Patent
McRae et al.

(10) Patent No.: US 11,266,434 B2
(45) Date of Patent: Mar. 8, 2022

(54) INTRODUCER SHEATHS, THROMBUS COLLECTION DEVICES, AND ASSOCIATED METHODS

(71) Applicant: Covidien LP, Mansfield, MA (US)

(72) Inventors: Robert Gordon McRae, Arvada, CO (US); Jessica Megan Clayton, San Jose, CA (US); James George Hanlon, Morgan Hill, CA (US); Lawrence Lee Go, San Jose, CA (US); Tim Ngoc Huynh, Milpitas, CA (US)

(73) Assignee: Covidien LP, Mansfield, MA (US)

( * ) Notice: Subject to any disclaimer, the term of this patent is extended or adjusted under 35 U.S.C. 154(b) by 636 days.

(21) Appl. No.: 16/148,560

(22) Filed: Oct. 1, 2018

(65) Prior Publication Data
US 2019/0029713 A1   Jan. 31, 2019

Related U.S. Application Data

(60) Continuation of application No. 14/482,217, filed on Sep. 10, 2014, now Pat. No. 10,130,387, which is a
(Continued)

(51) Int. Cl.
*A61B 17/3207* (2006.01)
*A61M 25/10* (2013.01)
(Continued)

(52) U.S. Cl.
CPC ............... *A61B 17/320725* (2013.01); *A61B 17/32075* (2013.01); *A61M 25/007* (2013.01); *A61M 25/0662* (2013.01); *A61M 25/10* (2013.01); *A61M 29/00* (2013.01); *A61B 2017/320741* (2013.01); *A61M 25/003* (2013.01);
(Continued)

(58) Field of Classification Search
CPC .......... A61M 25/0021; A61M 25/0023; A61M 25/0074; A61M 2025/0024; A61M 2025/0025; A61M 25/007; A61M 25/0662; A61M 25/10; A61M 29/00; A61M 25/003; A61M 2025/0037; A61M 2025/1061; A61F 2/01; A61F 2/013; A61F 2230/0067; A61F 2230/0091; A61B 17/320725; A61B 17/32075; A61B 2017/320741
See application file for complete search history.

(56) References Cited

U.S. PATENT DOCUMENTS 5,092,839 A   3/1992  Kipperman
5,102,415 A   4/1992  Guenther et al.
(Continued)

OTHER PUBLICATIONS

European Search Repod from counterpad European Application No. 11751154.3, dated May 6, 2014, 6 pp.
(Continued)

*Primary Examiner* — Julian W Woo
(74) *Attorney, Agent, or Firm* — Shumaker & Sieffert, P.A.

(57) ABSTRACT

A sheath comprises an elastomeric tube having a self-expanding scaffold coupled to a wall. The scaffold can expand to a diameter larger than the tube diameter to provide an enlarged distal opening. An aspiration catheter has a balloon and an aspiration port so that occlusive material can be removed from a blood vessel by drawing the balloon through the vessel while simultaneously aspirating through the port.

26 Claims, 23 Drawing Sheets

Related U.S. Application Data division of application No. 13/035,755, filed on Feb. 25, 2011, now abandoned.

(60) Provisional application No. 61/309,389, filed on Mar. 1, 2010, provisional application No. 61/385,637, filed on Sep. 23, 2010.

(51) Int. Cl.
*A61M 25/00* (2006.01)
*A61M 25/06* (2006.01)
*A61M 29/00* (2006.01)

(52) U.S. Cl.
CPC ............... *A61M 2025/0024* (2013.01); *A61M 2025/0037* (2013.01); *A61M 2025/1061* (2013.01)

(56) References Cited

U.S. PATENT DOCUMENTS

| | | | |
|---|---|---|---|
| 5,219,335 A | 6/1993 | Willard et al. | |
| 5,971,938 A | 10/1999 | Hart et al. | |
| 6,066,158 A * | 5/2000 | Engelson | A61B 17/221 606/159 |
| 6,159,230 A | 12/2000 | Samuels | |
| 6,210,370 B1 | 4/2001 | Chi-Sing et al. | |
| 6,292,633 B1 | 9/2001 | Nakagawa | |
| 6,331,184 B1 * | 12/2001 | Abrams | A61B 17/12022 604/164.09 |
| 6,425,909 B1 * | 7/2002 | Dieck | A61F 2/013 606/200 |
| 6,454,775 B1 | 9/2002 | Demarais et al. | |
| 6,511,492 B1 | 1/2003 | Rosenbluth et al. | |
| 6,544,276 B1 | 4/2003 | Azizi | |
| 6,635,070 B2 | 10/2003 | Leeflang et al. | |
| 6,695,858 B1 | 2/2004 | Dubrul et al. | |
| 6,695,977 B2 | 2/2004 | Prechtl et al. | |
| 6,755,813 B2 * | 6/2004 | Ouriel | A61F 2/013 604/537 |
| 6,808,520 B1 | 10/2004 | Fourkas et al. | |
| 6,929,633 B2 | 8/2005 | Evans et al. | |
| 6,932,830 B2 * | 8/2005 | Ungs | A61F 2/0108 606/200 |
| 6,936,025 B1 | 8/2005 | Evans et al. | |
| 6,945,977 B2 | 9/2005 | Demarais et al. | |
| 7,033,344 B2 | 4/2006 | Imran | |
| 7,141,045 B2 | 11/2006 | Johansson et al. | |
| 7,166,088 B2 | 1/2007 | Heuser | |
| 7,285,126 B2 | 10/2007 | Sepetka et al. | |
| 7,322,957 B2 * | 1/2008 | Kletschka | A61B 17/22032 606/198 |
| 7,344,515 B2 * | 3/2008 | Coyle | A61M 25/0082 604/104 |
| 7,410,491 B2 | 8/2008 | Hopkins et al. | |
| 7,476,232 B2 | 1/2009 | Deal | |
| 7,578,830 B2 | 8/2009 | Kusleika et al. | |
| 7,799,046 B2 | 9/2010 | White et al. | |
| 7,846,175 B2 | 12/2010 | Bonnette et al. | |
| 8,231,607 B2 * | 7/2012 | Takuma | A61B 17/22004 604/540 |
| 10,130,387 B2 | 11/2018 | McRae et al. | |
| 2002/0169436 A1 | 11/2002 | Gurm et al. | |
| 2002/0188276 A1 | 12/2002 | Evans et al. | |
| 2003/0004537 A1 * | 1/2003 | Boyle | A61F 2/013 606/200 |
| 2003/0176886 A1 | 9/2003 | Wholey et al. | |
| 2004/0219028 A1 | 11/2004 | Demarais et al. | |
| 2005/0038447 A1 | 2/2005 | Huffmaster | |
| 2005/0119686 A1 | 6/2005 | Clubb | |
| 2005/0222576 A1 | 10/2005 | Kick et al. | |
| 2006/0200184 A1 | 9/2006 | Deal | |
| 2006/0282155 A1 | 12/2006 | Fearn et al. | |
| 2007/0038241 A1 | 2/2007 | Pal | |
| 2007/0135832 A1 | 6/2007 | Wholey et al. | |
| 2007/0299465 A1 | 12/2007 | Messal et al. | |
| 2008/0249558 A1 | 10/2008 | Cahill | |
| 2010/0131000 A1 | 5/2010 | Demello et al. | |
| 2011/0264133 A1 | 10/2011 | Hanlon et al. | |

OTHER PUBLICATIONS

Prosecution History from U.S. Appl. No. 13/035,755, dated Nov. 9, 2012 through Jun. 25, 2014, 83 pp.

International Search Report and Written Opinion of International Application No. PCT/US11/026528, dated Apr. 27, 2011,7 pp.

International Preliminary Report on Patentability from International Application No. PCT/US11/026528, dated Sep. 4, 2012, 6 pp.

Communication Pursuant to Rules 161 (2) and 162 EPC dated Oct. 10, 2012, from counterpad European Application No. 11751154.3, 2 pp.

Prosecution History from U.S. Appl. No. 14/482,217, dated Oct. 6, 2016, through Jul. 9, 2018, 137 pp.

"F.A.S.T. Funnel Catheter, Proximal Occlusion Embolectomy/ Thrombectomy System: An Elegantly Simple Solution," Genesis Medical Interventional, accessed on Jul. 8, 2011, 4 pp.

\* cited by examiner

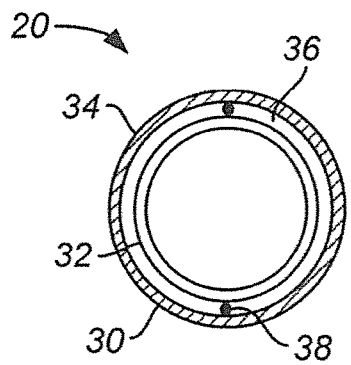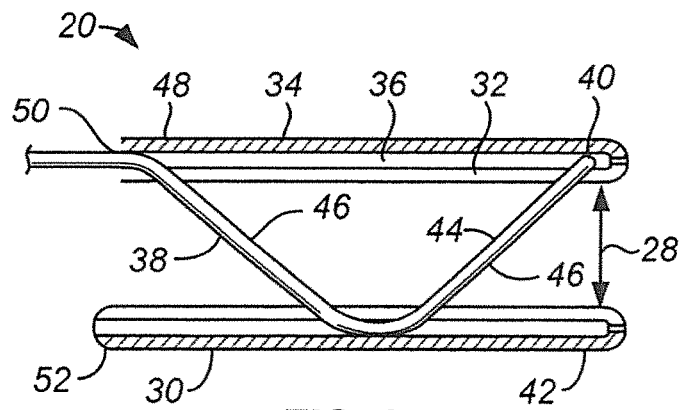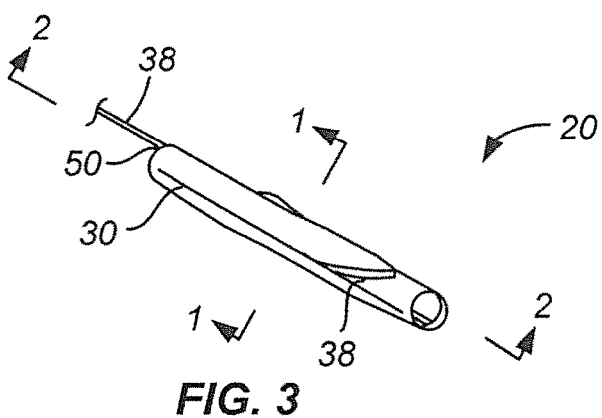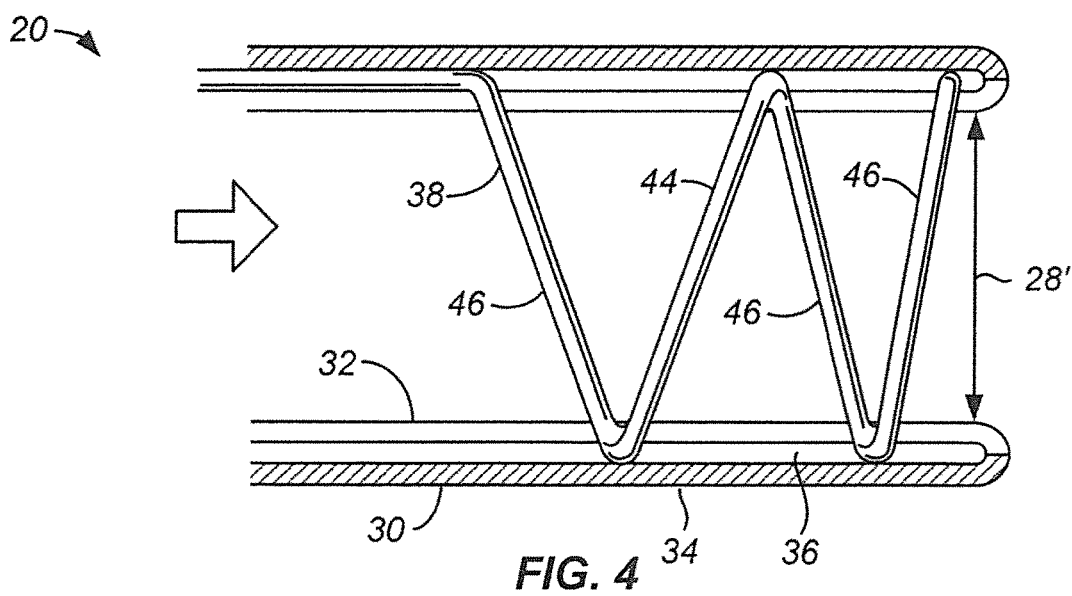

INTRODUCER SHEATHS, THROMBUS COLLECTION DEVICES, AND ASSOCIATED METHODS

CROSS-REFERENCE TO RELATED APPLICATIONS

This application is a continuation of application Ser. No. 14/482,217, filed Sep. 10, 2014, entitled, "INTRODUCER SHEATHS, THROMBUS COLLECTION DEVICES, AND ASSOCIATED METHODS," which is a divisional of application Ser. No. 13/035,755, filed on Feb. 25, 2011, entitled, "INTRODUCER SHEATHS, THROMBUS COLLECTION DEVICES, AND ASSOCIATED METHODS," which claims priority to provisional application Ser. No. 61/309,389, filed on Mar. 1, 2010, entitled, "RADIALLY COLLAPSIBLE AND EXPANDABLE INTRODUCER SHEATH AND THROMBUS COLLECTION DEVICE AND ASSOCIATED METHODS," and provisional application Ser. No. 61/385,637, filed on Sep. 23, 2010, entitled "INTRODUCER SHEATHS, THROMBUS COLLECTION DEVICES, AND ASSOCIATED METHODS," the entire content of each of which is hereby incorporated by reference and made a part of this disclosure.

BACKGROUND OF THE INVENTION

1. Field of the Invention

The present invention relates generally to medical devices and methods. More particularly, the present invention relates to apparatus for accessing vascular lumens and methods for clearing vascular lumens of occlusive materials.

Removing occlusive materials from the vasculature and other body lumens is the objective of many medical procedures. Obstructive materials in the vasculature include plaque, thrombus, embolus, clots, and fatty deposits. To remove such occlusive materials, catheters may be inserted into the occluded artery or vein for opening or removing the occlusive material. Of particular interest to the present invention, procedures commonly referred to as thrombectomy or embolectomy use a balloon-tipped catheter which is inserted into a blood vessel, either percutaneously or via a surgical cut down, where the balloon is advanced to a position distal to the obstructing material. After inflating the balloon, the catheter is drawn proximally to dislodge the material and remove it from the blood vessel. In some instances, a second sheath or catheter is introduced coaxially over the balloon-tipped catheter in order to apply suction and help remove the occlusive material before it is drawn out of the blood vessel.

When performing such thrombectomy or embolectomy procedures, the balloon-tipped catheters and other auxiliary tools may be introduced through a sheath which is positioned through a percutaneous tissue tract to allow access to the blood vessel. In addition, other auxiliary sheaths and tubular catheters may be employed and other aspects of the thrombectomy, embolectomy, or other vascular procedures.

While very effective, thrombectomy and embolectomy procedures sometimes have difficulty dislodging and removing certain occlusive materials from certain types of vessels. For example, the use of thrombectomy for removing plaque, clot and other occlusive buildups in arterio-venous grafts (AVG's) and arterio-venous fistulas (AVF's) can be particularly problematic. For example, a plug of occlusive materials frequently forms at the anastomosis site between the artery and vein, or artery and graft, and can be very difficult to remove. Moreover, the access sheaths and capture devices used in such procedures are not always optimal.

For these reasons, it would be desirable to provide improved methods and apparatus for performing thrombectomy and embolectomy procedures. It would be particularly desirable if such catheters and devices could improve the capture of clot, plaque, and other occlusive materials from AVG's and AVF's. Improved sheaths and other auxiliary devices for performing those procedures and others would also be desirable. At least some of these objectives will be met by the inventions described below.

2. Description of the Background Art

Thrombectomy devices employing aspiration are described in U.S. Pat. No. 6,292,633; U.S. 2002/0169436; U.S. Pat. Nos. 7,141,045; 7,033,344; 6,544,276; 7,578,830; 6,695,858; 6,210,370; 5,102,415; and 5,092,839. Catheters and sheaths having self-expanding regions are described in U.S. 2010/0131000; U.S. 2007/0135832; U.S. Pat. Nos. 7,799,046; 7,410,491; 6,511,492; 6,159,230; and 5,971,938.

SUMMARY OF THE INVENTION

One embodiment of the present radially collapsible and expandable sheath is configured for introducing an intravascular device into a patient's vasculature through a percutaneous access site. The sheath comprises an elongate, elastomeric, tubular casing including an inner layer and an outer layer defining an annular space therebetween. The casing has a distal end. The sheath further comprises an elongate wire. At least a portion of the wire occupies the annular space and forms a helix around the casing inner layer. The helix includes a plurality of coils. A distally directed force applied to the wire decreases a pitch between adjacent ones of the coils and radially expands the helix and the casing. A proximally directed force applied to the wire increases the pitch between adjacent ones of the coils and radially contracts the helix and the casing.

One embodiment of the present radially collapsible and expandable intravascular device is configured for removing a thrombus from a patient's vasculature through a percutaneous access site. The device comprises an elongate tubular catheter having a distal end. The device further comprises an elongate, elastomeric, tubular casing surrounding at least a portion of the catheter. The casing is secured to the catheter at or near the catheter distal end. The device further comprises an elongate wire. At least a portion of the wire occupies a space between the catheter and the casing and forms a helix around the catheter. The helix includes a plurality of coils. A distally directed force applied to the wire decreases a pitch between adjacent ones of the coils and radially expands the helix and the casing. A proximally directed force applied to the wire increases the pitch between adjacent ones of the coils and radially contracts the helix and the casing.

One embodiment comprises a system for removing a thrombus from a patient's vasculature through a percutaneous access site. The system includes the sheath described above in combination with the thrombus collection device described above.

One embodiment of the present methods for emplacing a radially collapsible and expandable sheath into a patient's vasculature through a percutaneous access site comprises a sheath including an elongate, elastomeric, tubular casing including an inner layer and an outer layer defining an annular space therebetween. The sheath further comprises an elongate wire, at least a portion of the wire occupying the annular space and forming a helix around the casing inner layer, the helix including a plurality of coils. The method comprises puncturing the patient's skin and vasculature with a catheter delivery needle in order to dispose a catheter within the patient's vasculature with a proximal end of the catheter protruding from the percutaneous access site. The method further comprises withdrawing the delivery needle. The method further comprises introducing the sheath, in a collapsed state, into the vasculature through a hollow lumen of the catheter. The method further comprises applying a distally directed force to the wire to decrease a pitch between adjacent ones of the coils and radially expand the helix and the casing so that the casing contacts interior walls of the vasculature. In certain embodiments, the method may further comprise applying a proximally directed force to the wire to increase a pitch between adjacent ones of the coils and radially collapse the helix and the casing.

One embodiment of the present methods for extracting a thrombus from a patient's vasculature through a percutaneous access site using a radially collapsible and expandable thrombus collection device comprises the device including an elongate tubular catheter having a distal end, an elongate, elastomeric, tubular casing surrounding at least a portion of the catheter. The device further comprises an elongate wire, at least a portion of the wire occupying a space between the catheter and the casing and forming a helix around the catheter, the helix including a plurality of coils. The method comprises emplacing a percutaneous introducer sheath into the patient's vasculature. The method further comprises introducing the thrombus collection device, in a collapsed state, by passing it through the sheath and into the patient's vasculature. The method further comprises advancing the device through the patient's vasculature toward a location of the thrombus by applying a distally directed force to a portion of the catheter that protrudes from the percutaneous access site. The method further comprises continuing to apply the distally directed force to push a distal end of the device through the thrombus. The method further comprises advancing the device through the thrombus until the casing has completely passed through the thrombus. The method further comprises expanding the wire and the casing by applying a distally directed force to the wire while holding the catheter stationary until at least a proximal end of the casing contacts an interior diameter of the vasculature. The method further comprises drawing the device back through the vasculature by applying a proximally directed force to the catheter while holding the wire stationary with respect to the catheter to maintain the casing in its expanded state. The method further comprises collecting the thrombus and trapping it within the space between the casing and the catheter as the device is drawn back. The method further comprises continuing to pull back on the catheter until the thrombus collection device reaches the distal end of the sheath. The method further comprises drawing the device through the sheath, together with the collected thrombus, until the device and the thrombus are completely extracted from the patient; and withdrawing the sheath from the percutaneous access site.

Another embodiment of the present methods for extracting a thrombus from a patient's vasculature through a percutaneous access site using a radially collapsible and expandable sheath and a radially collapsible and expandable thrombus collection device comprises the sheath including an elongate, elastomeric, tubular casing including an inner layer and an outer layer defining an annular space therebetween. The sheath further comprises an elongate wire, at least a portion of the sheath wire occupying the annular space and forming a helix around the casing inner layer, the sheath helix including a plurality of coils. The thrombus collection device includes an elongate tubular catheter having a distal end, an elongate, elastomeric, tubular casing surrounding at least a portion of the catheter, and an elongate wire. At least a portion of the device wire occupies a space between the catheter and the device casing and forms a helix around the catheter, the device helix including a plurality of coils. The method comprises puncturing the patient's skin and vasculature with a catheter delivery needle in order to dispose a delivery catheter within the patient's vasculature with a proximal end of the delivery catheter protruding from the percutaneous access site. The method further comprises withdrawing the delivery needle. The method further comprises introducing the sheath, in a collapsed state, into the vasculature through a hollow lumen of the delivery catheter. The method further comprises applying a distally directed force to the sheath wire to decrease a pitch between adjacent ones of the sheath coils and radially expand the sheath helix and the sheath casing so that the sheath casing contacts interior walls of the vasculature. The method further comprises introducing the thrombus collection device, in a collapsed state, by passing it through the sheath and into the patient's vasculature. The method further comprises advancing the device through the patient's vasculature toward a location of the thrombus by applying a distally directed force to a portion of the device catheter that protrudes from the percutaneous access site. The method further comprises continuing to apply the distally directed force to push a distal end of the device through the thrombus. The method further comprises advancing the device through the thrombus until the device casing has completely passed through the thrombus. The method further comprises expanding the device wire and the device casing by applying a distally directed force to the device wire while holding the device catheter stationary until at least a proximal end of the device casing contacts an interior diameter of the vasculature. The method further comprises drawing the device back through the vasculature by applying a proximally directed force to the device catheter while holding the device wire stationary with respect to the device catheter to maintain the device casing in its expanded state. The method further comprises collecting the thrombus and trapping it within the space between the device casing and the device catheter as the device is drawn back. The method further comprises continuing to pull back on the device catheter until the thrombus collection device reaches the distal end of the sheath. The method further comprises drawing the device through the sheath, together with the collected thrombus, until the device and the thrombus are completely extracted from the patient. The method further comprises applying a proximally directed force to the sheath wire to increase a pitch between adjacent ones of the sheath coils and radially collapse the sheath helix and the sheath casing. The method further comprises withdrawing the sheath from the percutaneous access site.

Another embodiment of the present introducer sheaths is configured for introducing an intravascular device into a patient's vasculature through a percutaneous access site. The sheath is elongate, tubular, and defines a sheath lumen. The sheath comprises a medial neck portion that flares outwardly to a wider bell portion at a distal end. The distal end of the bell portion is open. The neck portion and the bell portion comprise a compliant material. The bell portion of the sheath includes a wire that is encased within the compliant material. The wire supports the compliant material, maintaining the bell portion in its expanded shape when the sheath is unstressed. At a proximal end, the sheath includes a flush port that enables fluid to be injected and/or aspirated from the sheath lumen. Once deployed within the vasculature, a hemostasis valve at the proximal end of the sheath resists outflow of bodily fluids through the sheath.

One of the present embodiments comprises a deployment apparatus for an introducer sheath. The deployment apparatus includes a tubular dilator that is a rigid or semi-rigid component configured to guide the deployment apparatus through a skin puncture and through the vasculature. The dilator includes a proximal handle, a conically shaped distal tip, and defines a lumen that extends between the proximal and distal ends. The lumen is configured to receive a guide wire to facilitate introduction of the dilator into a patient. The introducer sheath is disposed coaxially about the outside of the dilator. An outer sheath is disposed coaxially about the outside of the introducer sheath. The outer sheath radially compresses the bell portion, which facilitates introduction of the sheath into the patient. The outer sheath is a tearaway sheath that can be torn by hand.

Another embodiment of the present methods comprises a method for deploying an introducer sheath in a patient's vasculature at a percutaneous access site using a deployment apparatus. The access site is prepared by puncturing the skin, any underlying tissue, and the vasculature with a needle. The operator then introduces a guide wire through the lumen of the needle, and withdraws the needle. The method further comprises the operator introducing the deployment apparatus into the vasculature through the puncture site using the guide wire. The operator advances the apparatus through the puncture site and the vasculature until a bell portion of the sheath is located entirely within the vasculature and a neck portion traverses the puncture site. The operator next removes a tearaway outer sheath from the deployment apparatus and pulls the outer sheath through the puncture site. The operator then removes a dilator of the apparatus.

Another embodiment of the present intravascular devices is configured for removing a thrombus from a patient's vasculature through a percutaneous access site. The device comprises an aspiration catheter including an elongate body having a balloon at its distal end. The catheter body comprises a flexible material having sufficient rigidity to facilitate guiding the catheter through the vasculature from the proximal end. The body defines two radially spaced lumens that are not in fluid communication with one another. The first lumen is an aspiration lumen that extends from an aspiration connector at the proximal end of the catheter to a plurality of aspiration openings toward the distal end of the catheter. The second lumen is an inflation lumen that extends from an inflation connector at the proximal end of the catheter to the balloon toward the distal end of the catheter. The aspiration lumen has a larger diameter than the inflation lumen, and is configured for passage of thrombus.

Another embodiment of the present methods comprises a method for percutaneously removing a thrombus from a patient's vasculature. The method comprises introducing an aspiration catheter into a patient's vasculature through an introducer sheath. The aspiration catheter is then advanced distally through the sheath, the vasculature, and the thrombus until a balloon of the catheter is disposed on the far side of the thrombus. A guide wire may be used to advance the catheter. The method further comprises connecting a syringe filled with inflation liquid to an inflation connector of the catheter. The operator depresses the syringe plunger to force the inflation liquid into the balloon through an inflation lumen. The operator inflates the balloon until it presses against the interior walls of the vasculature on the far side of the thrombus. The operator moves a stopcock to a position to prevent liquid flow through the inflation connector and disconnects the syringe from the stopcock. The operator removes the thrombus from the vasculature by using a combination of suction through the aspiration openings, and proximal movement of the inflated balloon across the thrombus. To do so, the operator connects a Luer stopcock to an aspiration connector and an empty syringe to the stopcock. To generate suction, the operator draws back on the syringe plunger with the stopcock in the closed position and then locks the plunger. The operator then draws the catheter out of the vasculature while simultaneously moving the stopcock to the open position, thereby exposing the vacuum in the syringe barrel to the aspiration lumen, generating suction that pulls pieces of the thrombus into the aspiration lumen through the aspiration openings. The operator continues to pull back on the aspiration catheter until all or substantially all of the thrombus has been pulled into the sheath. The operator then continues to pull back on the aspiration catheter to force the thrombus out of the vasculature through the sheath.

Thus, in a first aspect of the present invention, a sheath comprises a tubular body having a proximal, a distal end, and an axial passage therethrough. The tubular body is formed at least partially from an elastomeric material so that it can be collapsed, be expanded to a fully open configuration where it has an open diameter, and be further expanded beyond the open diameter by applying a radially outward force to an internal surface of the tubular body. The sheath further comprises a self-expanding scaffold coupled to at least a portion of the tubular body. The self-expanding scaffold also has a collapsed configuration, an expanded diameter when free from external constraint, and a super-expanded diameter or width when subject to a radially outward inner force. The expanded diameter of the self-expanding scaffold will be at least as large as the open diameter of the tubular body, optionally being larger. In this way, the scaffold will be able to open the tubular body. For example, the scaffold could be present only at the distal end of the tubular body so that said distal end will remain open while the remainder of the tubular body could remain in a collapsed configuration.

Optionally, the sheath will further comprise a shaft extending from the proximal end of the tubular body. In many instances, the shaft will comprise an extension of the scaffold. For example, the scaffold may be in the form of a helical coil where the shaft is an integral extension of the coil. That is, the shaft and coil may be formed from a single wire, filament, bundle or other structure where only a distal portion of the structure is formed into the coil to act as the scaffold while the remaining proximal portion of the structure can act as the shaft.

In most instances, the scaffold will have a cylindrical geometry when expanded, but in other instances the scaffold may have a tapered geometry when expanded. For example, the scaffold may be configured so that it tapers to a more narrow configuration in the distal direction. In such instances, the scaffold can form the tubular body into a capturing element for withdrawing clot.

In still other embodiments, the sheath may further comprise a catheter body where the sheath and scaffold are disposed over a distal end of the catheter body. Optionally, a shaft of the sheath may then extend through a lumen of the catheter body to allow selective opening and closing of the sheath over the catheter by translating the shaft forwardly or distally.

In specific embodiments, the self-expanding scaffold may be embedded in a wall of the sheath. Alternatively, the self-expanding scaffold may be secured to an inner or outer surface of a wall of the sheath. In a still further alternative embodiment, the self-expanding scaffold may be disposed in an annular space formed or created in a wall of the sheath so that the scaffold can foreshorten as it expands without constricting or deforming the wall (other than any radial expansion that may occur).

The sheath will have dimensions typical for medical sheaths. Typically, the tubular body will have an expanded diameter in the range from 3 Fr. to 24 Fr., the self-expanding scaffold will have a diameter in the range from 3 Fr. to 38 Fr. and the sheath will have a length in the range from 10 cm to 200 cm.

In a further aspect of the present invention, methods for aspirating occlusive material from a patient's vasculature comprise providing a catheter including a shaft, an expandable member at a distal end of the shaft, and an aspiration port on the shaft proximal to the expandable member. The aspiration port is connected to an aspiration lumen extending to a proximal end of the shaft. The catheter is introduced to a blood vessel (including implanted grafts and created fistulas) so that the expandable member lies on a distal side of the occlusive material. The expandable member is then expanded, and the catheter is drawn proximal while aspirating through the lumen end port to remove the occlusive material from the vessel. The methods of the present invention may be used in any blood vessel, but will find particular use with peripheral blood vessels, arterio-venous grafts, arterio-venous fistulas, and the like.

In the preferred embodiments, the catheter will consist of only a single balloon at a distal end of the catheter shaft and further preferably will consist of only a single aspiration port located proximally of the balloon, typically at a distance from 5 mm to 3 cm. Usually, the drawing and aspiration steps are performed simultaneously and are able together to remove substantially all the occlusive material. In other instances, however, some portion of the occlusive material will be drawn proximally without being aspirated through the port and lumen and will be removed from the vessel, graft, or fistula through an access sheath and/or a capturing catheter.

BRIEF DESCRIPTION OF THE DRAWINGS

FIG. 1 is a cross-sectional end view of one embodiment of the present radially collapsible and expandable introducer sheath, taken along the line 1-1 in FIG. 3, and illustrating the sheath in a collapsed state;

FIG. 2 is a cross-sectional side view of the sheath of FIG. 1, taken along the line 2-2 in FIG. 3;

FIG. 3 is an end/side perspective view of the sheath of FIG. 1;

FIG. 4 is a cross-sectional side view of the sheath of FIG. 1, taken along the line 4-4 in FIG. 5, and illustrating the sheath in an expanded state;

DETAILED DESCRIPTION OF THE INVENTION

Figure 5:
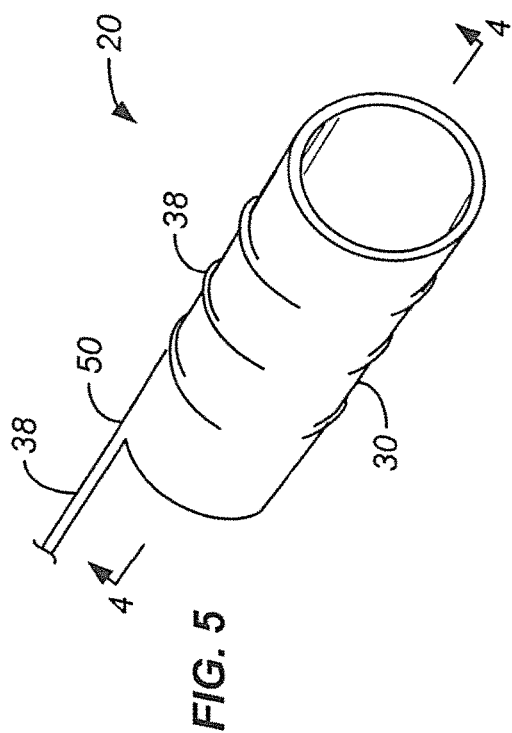
FIG. 5 is an end/side perspective view of the sheath of FIG. 4.

The following detailed description describes the present embodiments with reference to the drawings. In the drawings, reference numbers label elements of the present embodiments. These reference numbers are reproduced below in connection with the discussion of the corresponding drawing features. The various embodiments of the present introducer sheaths, thrombus collection devices and associated methods now will be discussed in detail. These embodiments include the introducer sheaths and thrombus collection devices shown in the accompanying drawings, which are for illustrative purposes only.

Some embodiments of the present introducer sheaths, thrombus collection devices and associated methods are described below with reference to the figures. These figures, and their written descriptions, indicate that certain components of the apparatus are formed integrally, and certain other components are formed as separate pieces. Components shown and described herein as being formed integrally may in alternative embodiments be formed as separate pieces. Components shown and described herein as being formed as separate pieces may in alternative embodiments be formed integrally. Further, as used herein the term integral describes a single unitary piece.

Figure 6:
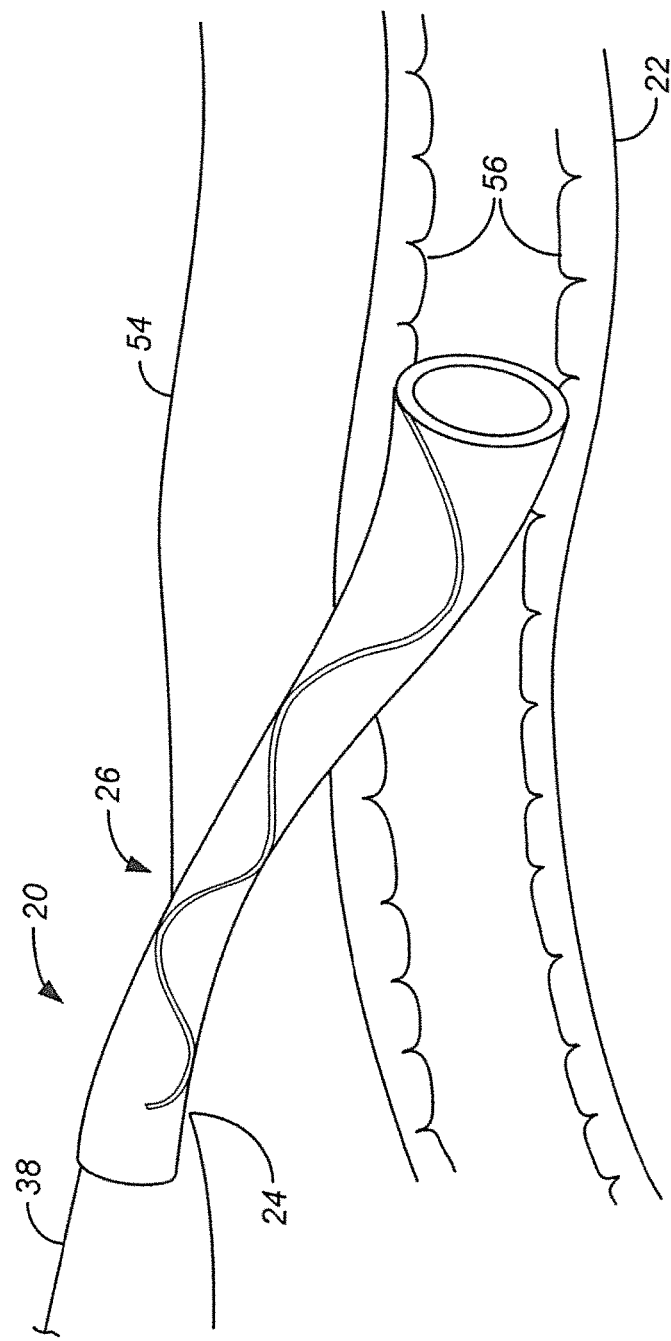
FIG. 6 is a partial cross-sectional side view of the sheath of FIGS. 1-5 disposed in a patient's vasculature at a percutaneous access site.

FIGS. 1-6 illustrate one embodiment of the present radially collapsible and expandable sheath 20. As shown in FIG. 6, the sheath 20 is configured for passage into a patient's vasculature 22 (e.g. in a vein or artery, an arterio-venous fistula (AVF) or arterio-venous graft (AVG), or alternatively in a non-vascular location such as the peritoneal cavity or other bodily cavities or hollow anatomical structures) through an opening 24 at a percutaneous access site 26. Once deployed as shown in FIG. 6, the sheath 20 can be used as a conduit for introducing one or more intravascular devices into the patient's vasculature 22. For example, and as discussed further below, in one embodiment the sheath 20 can be used to introduce a thrombectomy device.

FIGS. 1-3 illustrate the sheath 20 in a collapsed or contracted state. FIGS. 4 and 5 illustrate the sheath 20 in an expanded state. An operator may readily expand and contract the sheath 20 in the radial direction to increase or decrease its internal diameter 28, 28', respectively. For example, the internal diameter 28, 28' may be increased for the passage of intravascular devices, and decreased to promote hemostasis at the percutaneous access site 26, as discussed further below.

With reference to FIGS. 1-3, the sheath 20 comprises an elongate, elastomeric, tubular casing 30. As shown in the cross-sectional views of FIGS. 1 and 2, the tubular casing 30 includes an inner layer 32 and an outer layer 34. The layers 32, 34 define an annular space 36 between them. The annular space 36 receives a portion of an elongate wire 38 that an operator may manipulate to expand and contract the casing 30, as described in detail below.

With particular reference to FIG. 2, a distal end 40 of the wire 38 is disposed within the annular space 36 at or near a distal end 42 of the casing 30. In one embodiment, the distal end 40 of the wire 38 may be secured to the casing 30. In an alternative embodiment, the distal end 40 of the wire 38 may be freely movable with respect to the inner layer 32 and the outer layer 34. The distal end 40 of the wire 38 may include a blunt cap (not shown) to reduce the likelihood of the wire 38 puncturing the elastomeric casing 30.

Proximal of the wire 38 distal end 40, the wire 38 forms a helix 44. The helix 44 includes a plurality of coils 46 that wrap around the casing inner layer 32 beneath the casing outer layer 34. The helix 44 extends to a proximal end 48 of the casing 30 where the wire 38 extends through an opening 50 in the casing 30. As indicated by the break lines in FIGS. 2 and 3, the wire 38 may have any desired length extending proximally of the casing 30. As explained in further detail below, an operator may manipulate the proximal end of the wire 38 to force more of the wire 38 into the annular space 36 through the opening 50, or to withdraw some of the wire 38 from the annular space 36 through the opening 50. This manipulation expands and contracts the helix 44 and the casing 30, as described below.

As described above, the casing 30 may comprise a compliant material. As used herein, the term compliant should be understood to include at least the following properties: flexibility, elasticity, and collapsibility/expandability. Further, because the casing 30 is configured for use internally, the material is preferably biocompatible. Example materials for the casing 30 include silicone film, polyisoprene, TECOTHANE®, PELLETHANE®, and other materials having similar properties.

The wire 38 preferably comprises a material that is flexible but incompressible. Further, because the wire 38 is configured for use internally, the material is preferably biocompatible. Example materials for the wire 38 include nickel-titanium (NiTi) alloys, stainless steel, polyether ether ketone (PEEK) and other materials having similar properties.

Again, FIGS. 1-3 illustrate the sheath 20 in a collapsed or contracted state. In this state, a relatively small portion of the wire 38 is disposed within the annular space 36. However, when the flexible but incompressible wire 38 is subjected to a compressive force applied proximally of the casing 30, wire 38 is forced into the annular space 36 through the opening 50 where the wire 38 enters the casing 30. As more wire 38 enters the annular space 36, the wire 38 forms tighter and more closely-spaced coils 46 within the helix 44, with the coils 46 having increasingly larger diameters, as shown in FIGS. 4 and 5. The elastomeric nature of the casing 30 makes it readily expandable in the radial direction as the wire 38 forces it outward. Similarly, when the wire 38 is subjected to a tensile force applied proximally of the opening 50, the coils 46 within the helix 44 relax and spread apart as wire 38 is drawn out of the opening 50. Again, the elastomeric nature of the casing 30 makes it readily contractible in the radial direction as the radial support provided by the wire 38 diminishes.

In the illustrated embodiment, the wire 38 is freely slidable within the annular space 36 with respect to the inner layer 32 and the outer layer 34. Thus, as the wire 38 is forced into the annular space 36 through the opening 50, the helix 44 slides against the inner and outer layers 32, 34 to enable the casing 30 to expand without forming pleats between adjacent coils 46. The expanded sheath 20 thus presents a relatively smooth inner diameter 28' for easy passage of intravascular devices. However, in alternative embodiments the wire 38 may be secured to the casing 30 at one or more locations.

As shown in FIGS. 2 and 4, the inner and outer layers 32, 34 of the casing 30 preferably converge at the proximal end 52, and at the distal end 42, thereby sealing the proximal and distal ends 42, 52 of the annular space 36. The inner and outer layers 32, 34 may, for example, be formed integrally. The sealed proximal end 52 of the annular space 36 facilitates controlled insertion and withdrawal of the wire 38 through the opening 50. The sealed distal end 42 of the annular space 36 resists movement of the wire 38 distally out of the annular space 36. The sealed distal end 42 can also form a smooth, atraumatic leading edge of the casing 30 to facilitate transport of material into the distal opening of the sheath 20 while avoiding injury to blood vessel walls or other nearby anatomy.

FIG. 6 illustrates the sheath 20 positioned in a patient's vasculature 22 through an opening 24 at a percutaneous access site 26. The sheath 20 may be deployed in this configuration using, for example, a catheter (not shown). An operator may puncture the patient's skin 54 and vasculature 22 with a catheter delivery needle (not shown) in order to dispose the catheter within the patient's vasculature 22 with a proximal end of the catheter protruding from the percutaneous access site 26, e.g. via the Seldinger technique or any other suitable access technique. The operator may then introduce the sheath 20 into the vasculature 22 through the catheter lumen and then withdraw the catheter over the sheath 20, leaving the sheath 20 in the state shown in FIG. 6. Alternatively, the operator can insert the sheath 20 over a guidewire emplaced via the Seldinger technique. For ease of insertion, the operator would typically introduce the sheath 20 in its collapsed state (FIGS. 1-3). Upon emplacement, the operator may thereafter expand the sheath 20 to the configuration shown in FIG. 6 so that it achieves wall-to-wall apposition with the interior walls 56 of the vasculature 22. The operator expands the sheath 20 by applying a distally directed force to the wire 38 as described above. Further expansion of the sheath 20 may facilitate removing thrombus from the vasculature 22, as explained further below.

Once the sheath 20 is emplaced as shown in FIG. 6, it is configured to provide an access path to the vasculature 22 for various intravascular devices. In one procedure described below, the sheath 20 is used to introduce a device for removing a thrombus. The sheath 20 can be used as an introducer for any type of intravascular device. The example described below is not limiting.

The expandable and contractible nature of the sheath 20 allows it to accommodate devices of various sizes. For example, the sheath 20 may be expanded to such an extent that it also radially expands the vasculature 22, allowing for passage of a particularly large device or thrombus. Further, when another device is not disposed through the interior of the sheath 20, the sheath 20 may be contracted to tighten the percutaneous access opening 24. This contraction aids hemostasis, reducing the tendency of blood to flow outward from the percutaneous access opening 24. The contraction can occur "automatically" without requiring action by the operator, resulting from the natural compliance and collapsibility of the sheath. The subcutaneous tissues surrounding the sheath 20 can exert sufficient pressure on the sheath 20 to contract the sheath and/or force it closed entirely, or otherwise force the sheath walls into close contact with any object(s) in the sheath lumen. When the intravascular procedure is complete, the operator may contract the sheath 20 and withdraw it from the percutaneous access opening 24. The operator contracts the sheath 20 by applying a proximally directed force to the wire 38 as described above.

FIGS. 7-10 illustrate one embodiment of the present radially collapsible and expandable thrombus collection device 60. As described further below, the device 60 is configured to be inserted into a patient's vasculature through an introducer sheath that passes through an opening at a percutaneous access site. When inserted in a collapsed state, the device 60 can be advanced past the thrombus, expanded, and then drawn back to pull the thrombus away from the interior of the vasculature and trap the thrombus within the device 60. As the expanded device 60 is withdrawn further, it pulls the thrombus proximally through the introducer sheath until it eventually exits the vasculature through the percutaneous opening. This procedure is described further below.

Figure 7:
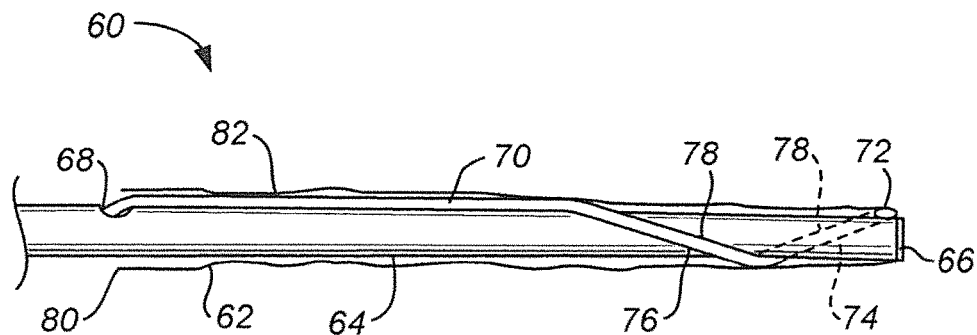
FIG. 7 is a side elevation view of one embodiment of the present collapsible and expandable thrombus collection device, illustrating the device in a collapsed state.
Figure 8:
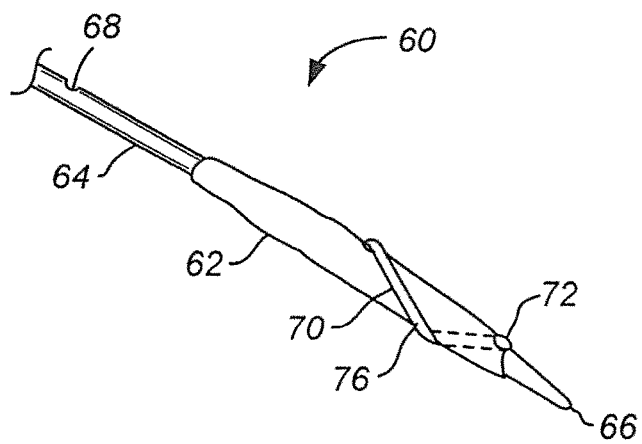
FIG. 8 is an end/side perspective view of the device of FIG. 7.
Figure 10:
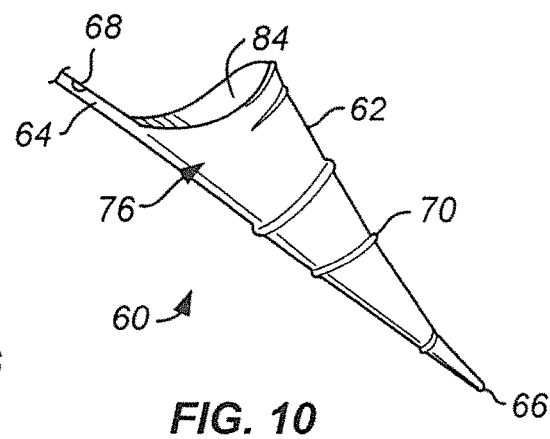
FIG. 10 is an end/side perspective view of the device of FIG. 9.
Figure 9:
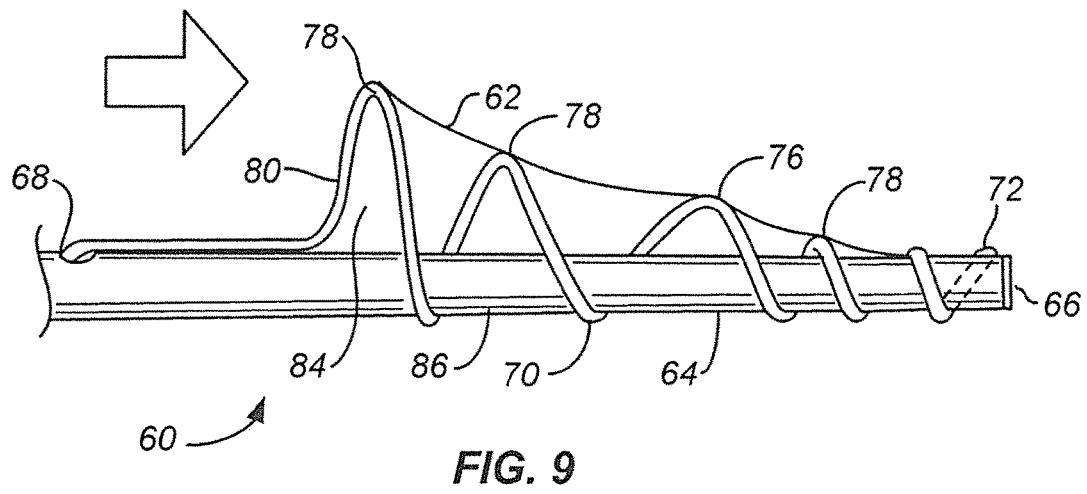
FIG. 9 is a side elevation view of the device of FIG. 7, illustrating the device in an expanded state.

FIGS. 7 and 8 illustrate the device 60 in a collapsed or contracted state. FIGS. 9 and 10 illustrate the device 60 in an expanded state. An operator may readily expand and contract the device 60 in the radial direction to increase or decrease its external diameter. For example, the external diameter may be decreased to enable the device 60 to pass freely through the introducer sheath. Once deployed in the vasculature, the external diameter may be increased to contact the interior diameter of the vasculature, thereby matching the diameter of a thrombus.

With reference to FIGS. 7 and 8, the thrombus collection device 60 comprises an elongate, elastomeric, tubular casing 62. As shown in the side elevation view of FIG. 7, the tubular casing 62 extends over a tubular catheter 64 from a distal end 66 of the catheter 64 to a point distal of an opening 68 in the sidewall of the catheter 64. A space between the catheter 64 and the casing 62 receives a portion of an elongate wire 70 that an operator may manipulate to expand and contract the casing 62, as described in detail below. While FIG. 7 is not a cross-sectional view, the catheter 64 and the wire 70 are shown beneath the casing 62 for clarity.

With continued reference to FIG. 7, a distal end 72 of the wire 70 is disposed at or near a distal end 66 of the catheter 64. For clarity, a distal portion 74 of the wire 70 that is positioned on the far side of the catheter 64 is shown in hidden lines. In one embodiment, the distal end 72 of the wire 70 may be secured to the catheter 64. In an alternative embodiment, the distal end 72 of the wire 70 may be freely movable with respect to the catheter 64 and the casing 62. The distal end 72 of the wire 70 may include a blunt cap (not shown) to reduce the likelihood of the wire 70 puncturing the elastomeric casing 62.

Proximal of the wire distal end 72, the wire 70 forms a helix 76. The helix 76 includes a plurality of coils 78 that wrap around the catheter 64 beneath the casing 62. The wire 70 extends past a proximal end 80 of the casing 62 and then through the opening 68 in the catheter 64. The wire 70 extends through the interior of the catheter 64 proximal of the opening 68, exiting through a proximal end of the catheter lumen. In an alternative embodiment, the catheter 64 may omit the opening 68, so that the wire 70 is always disposed externally of the catheter 64. Further, the wire 70 may have any desired length extending proximally of the casing 62 and/or catheter 64. As explained in further detail below, an operator may manipulate the proximal end of the wire 70 to force the wire 70 to expand and contract radially in a fashion similar to that described above with respect to the sheath 20.

The casing 62 and the wire 70 preferably comprise material properties corresponding to those described above with respect to the casing 30 and the wire 38 of the sheath 20. Further, the example materials described with respect to the sheath 20 can also be implemented in the present thrombus collection device 60.

The catheter 64 preferably comprises a material that is flexible but rigid enough to support the casing 62 and the wire 70 as the device 60 is inserted into a patient's vasculature through an introducer sheath, and also rigid enough to support the casing 62 and the wire 70 as those components radially expand and contract. Further, because the catheter 64 is configured for use internally, the material is preferably biocompatible. Example materials for the catheter 64 include various thermoplastics such as polyimide, fluorinated ethylene propylene (FEP), PEBAX, and other materials having similar properties.

Again, FIGS. 7 and 8 illustrate the device 60 in a collapsed or contracted state. In this state, the wire 70 includes a relatively straight portion 82 extending between the opening in the catheter 64, and a helical portion distal of the straight portion 82. However, when the flexible but incompressible wire 70 is subjected to a compressive force applied proximally of the opening 68, the wire 70 is forced distally in the space between the casing 62 and the catheter 64. As the wire 70 moves distally, it forms tighter coils 78 within the helix 76, with the coils 78 having increasingly larger diameters, as shown in FIGS. 9 and 10. The elastomeric nature of the casing 62 makes it readily expandable in the radial direction as the wire 70 forces it outward. The expanded casing 62 presents a wide proximal opening 84 to the space between the casing 62 and the catheter 64. Similarly, when the wire 70 is subjected to a tensile force applied proximally of the opening 68, the coils 78 within the helix 76 relax as wire 70 is pulled proximally, collapsing the wire 70 and the casing 62 and narrowing the proximal opening 84. Again, the elastomeric nature of the casing 62 makes it readily contractible in the radial direction as the radial support provided by the wire 70 diminishes.

In one embodiment, the wire 70 is freely slidable within the space between the casing 62 and the catheter 64. Thus, as the wire 70 is forced distally, additional wire 70 is forced into the space between the casing 62 and the catheter 64. The helix 76 slides against the casing 62 and the catheter 64 as it expands radially to enable the casing 62 to expand without forming pleats between adjacent coils 78. The expanded sheath thus presents a relatively smooth outer diameter for easy passage of the device 60 within the patient's vasculature. However, in alternative embodiments the wire 70 may be secured to the casing 62 at one or more locations, such as at the proximal end 80 of the casing 62.

As shown in FIGS. 9 and 10, the illustrated embodiment of the thrombus collection device 60 expands to form a substantially conical shape, or any other suitable shape, including any tapering shape with a proximal open end and a smaller, closed distal end. To achieve this expanded shape, the casing 62 may, for example, be secured to the catheter 64 at one or more locations along a straight line that traces the outer surface of the catheter 64. In the illustrated embodiment, this line is along the lower side 86 of the catheter 64. Because the casing 62 is attached to the catheter 64, as the wire 70 is forced distally under an applied force the wire 70 and the casing 62 are constrained against expansion on the side 86 of the catheter 64 where the casing 62 is attached, causing the casing 62 to assume a generally conical or elongate conical shape as it expands. The conical expanded shape achieves advantages for thrombus collection, as described in further detail below.

Figure 11:
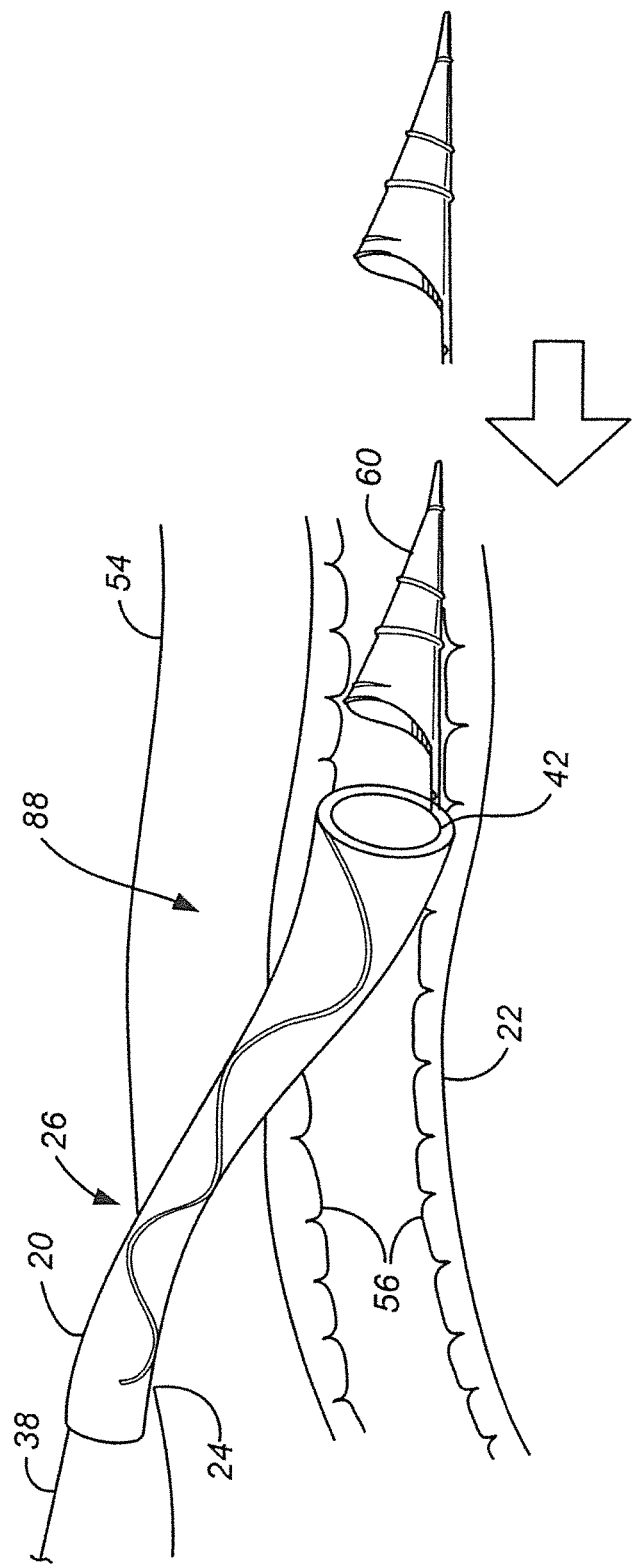
FIG. 11 is a partial cross-sectional side view of the sheath of FIGS. 1-6 in combination with the device of FIGS. 7-10.

FIGS. 11-15 illustrate one method of using the thrombus collection device 60 of FIGS. 7-10 to perform a thrombectomy. As shown in FIG. 11, the thrombus collection device 60 may be combined with the sheath 20 of FIGS. 1-6 to form a system 88 for performing a thrombectomy. However, the present thrombus collection device 60 may be used with any introducer sheath. Thus, the present sheath 20 and thrombus collection device 60 are each usable separately, or in combination.

With reference to FIG. 11, a process for extracting a thrombus begins with the operator emplacing the sheath 20 as described above with respect to FIG. 6. The operator can then expand the sheath 20 by applying a distally directed force to the sheath wire 38. With the sheath 20 expanded, the operator introduces the thrombus collection device 60 by passing it through the expanded sheath 20 and into the patient's vasculature 22, as shown in FIG. 11. To aid introduction, the operator would typically introduce the thrombus collection device 60 in its collapsed state (FIGS. 7 and 8). FIG. 11, however, illustrates the device wire 70 and the device casing 62 in their expanded states for clarity. Once the device 60 has been introduced into the vasculature 22, the operator may collapse the sheath 20 by applying a proximally directed force to its wire 38. In the collapsed state, the sheath 20 advantageously promotes hemostasis at the percutaneous access site 26 by allowing the percutaneous puncture 24 to reduce in size. The collapsed sheath 20, however, still provides an adequate inside diameter to enable the thrombus collection device 60 to be manipulated within the vasculature 22. The step of collapsing the sheath 20 is optional.

Figure 12:
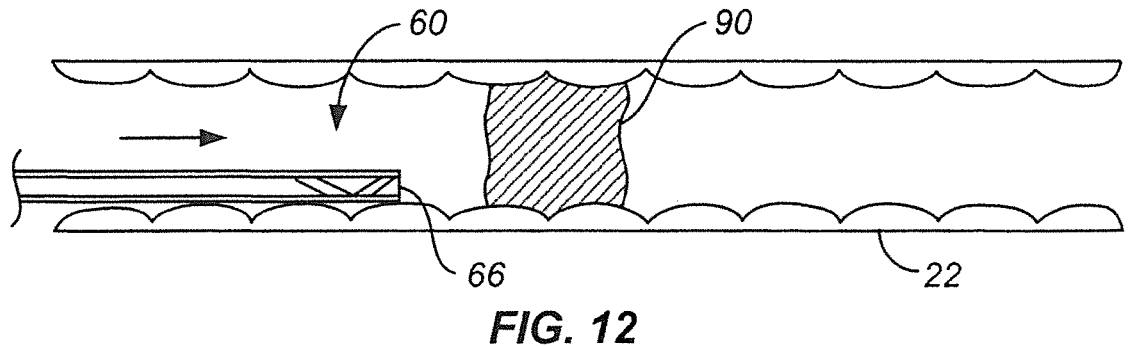
FIG. 12 is a partial cross-sectional side view of the device of FIGS. 7-10 disposed in a patient's vasculature during a thrombectomy procedure.

With reference to FIG. 12, the operator advances the device 60 through the patient's vasculature 22 toward the location of the thrombus 90. The operator may advance the device 60 by applying a distally directed force to the portion of the catheter 64 that protrudes from the percutaneous access site 26. The operator may use a guide wire (not shown) and/or imaging, such as ultrasound, to assist in guiding the device 60 through the vasculature 22 to the thrombus 90.

Figure 13:
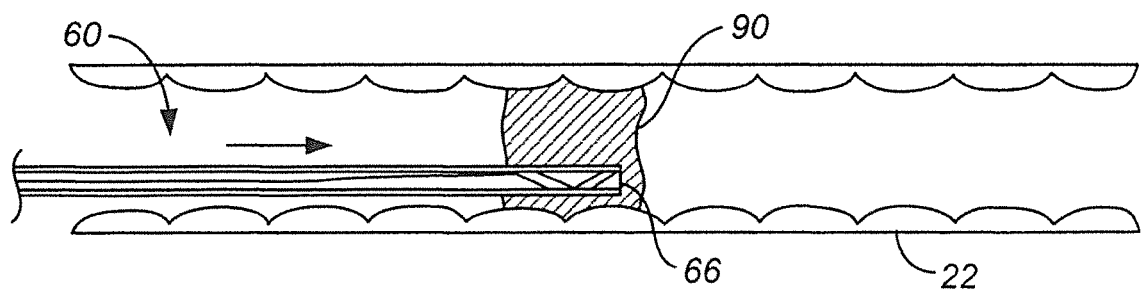
FIG. 13 is a partial cross-sectional side view of the device of FIGS. 7-10 disposed in a patient's vasculature during a thrombectomy procedure.

When the thrombus collection device 60 reaches the thrombus 90, as shown in FIG. 13, the operator continues applying distally directed force to push the distal end 66 of the device 60 through the thrombus 90. The present thrombus collection device 60 is configured to collect acute thrombi, which typically have a gelatin-like consistency. The operator may thus typically pass the device 60 through the thrombus 90 without substantial difficulty. The moderate rigidity of the catheter 64 and the low profile of the device 60 aid in penetrating the thrombus 90.

Figure 14:
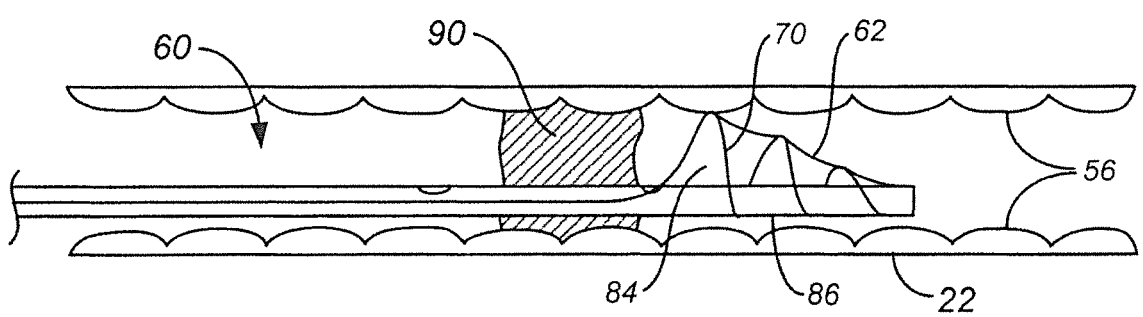
FIG. 14 is a partial cross-sectional side view of the device of FIGS. 7-10 disposed in a patient's vasculature during a thrombectomy procedure.

The operator continues advancing the device 60 through the thrombus 90 until the device casing 62 has completely passed through the thrombus 90. The operator then expands the device wire 70 and the device casing 62 as shown in FIG. 14. The operator expands the device wire 70 and the device casing 62 by applying a distally directed force to the device wire 70 while holding the catheter 64 stationary. The operator may expand the device wire 70 and the device casing 62 until achieving wall-to-wall apposition with the interior diameter 56 of the vasculature. The operator may use imaging and/or tactile feedback to determine when the device casing 62 is expanded to the desired amount.

Figure 15:
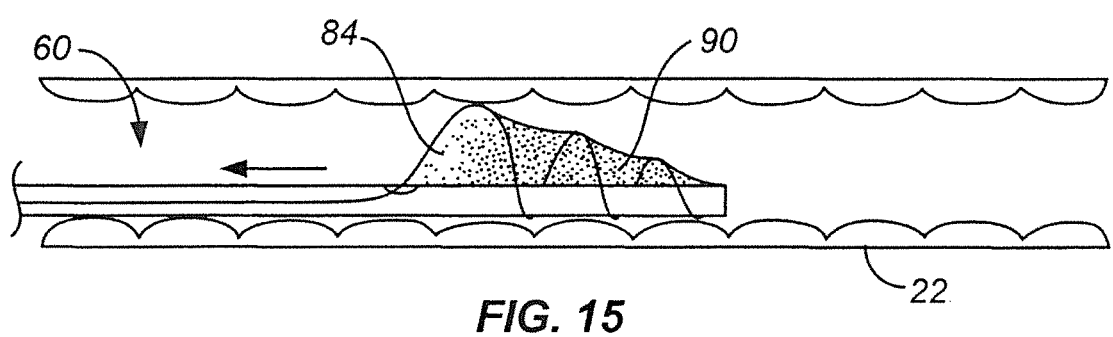
FIG. 15 is a partial cross-sectional side view of the device of FIGS. 7-10 disposed in a patient's vasculature during a thrombectomy procedure.

With the device casing 62 expanded and positioned distally of the thrombus 90, the operator draws the device 60 back through the vasculature 22 by applying a proximally directed force to the catheter 64 while holding the device wire 70 stationary with respect to the catheter to maintain the device casing 62 in its expanded state. As the expanded device 60 is pulled proximally, the proximal opening 84 of the device casing 62 collects the thrombus 90 and traps it within the space between the device casing 62 and the catheter 64, as shown in FIG. 15. The operator continues to pull back on the catheter 64 until the thrombus collection device 60 reaches the distal end 42 of the sheath 20, as shown in FIG. 11. Again, the operator may use imaging to determine the location of the thrombus collection device 60. As illustrated, in FIGS. 12-15, the operator may advantageously advance the device 60 through the thrombus 90 such that the line 86 along which the device casing 62 is attached to the catheter 64 faces the interior wall 56 of the vasculature 22. Thus, when the conical device casing 62 is expanded, its proximal opening 84 is positioned to completely engulf the thrombus 90 when pulled back.

When the thrombus collection device 60 reaches the distal end 42 of the sheath 20, as shown in FIG. 11, the operator draws the device 60 through the sheath 20, together with the collected thrombus 90, until the device 60 and the thrombus 90 are completely extracted from the patient. To aid in extraction, the operator would typically expand the sheath 20 prior to withdrawing the device 60 so that the sheath 20 may better accommodate the expanded device 60. The sheath 20 may advantageously be expanded over a wide range, so that it can for example be expanded to contact the interior diameter 56 of the vasculature 22, and be expanded even farther to radially expand the vasculature 22. This increased expansion is advantageous for withdrawing the thrombus collection device 60, as the thrombus collection device 60 may sometimes be expanded during withdrawal to a diameter that is substantially equal to the interior diameter of the vasculature 22. Optionally, the operator can rely upon the natural expandability of the sheath 20, rather than or in addition to manual expansion of the sheath, to expand the sheath 20 in response to the introduction of a large-diameter object (e.g. the device 60 containing a relatively large portion of thrombus) into the sheath lumen. Upon withdrawing the thrombus collection device 60, the operator may thereafter collapse the sheath 20 and also withdraw it from the percutaneous access site 26. Just before or during withdrawal of the device 60, the operator can pull the device wire 70 proximally so that the wire 70 serves as a clamp or drawstring that holds the collected thrombus in the casing 62 or wire coils more securely during withdrawal.

Figure 16:
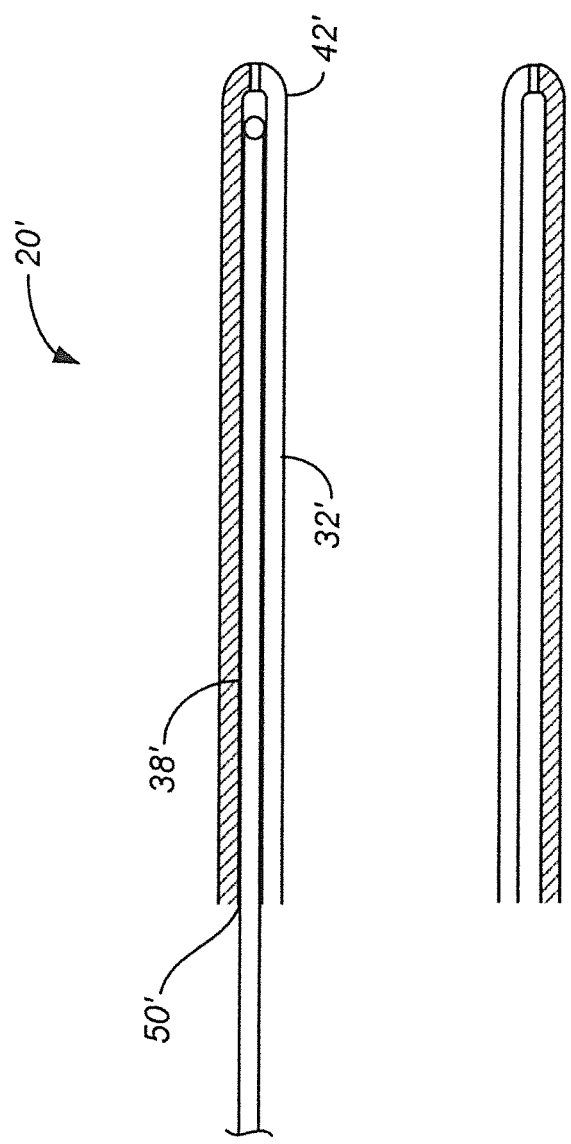
FIG. 16 is a cross-sectional side view of another embodiment of the present radially collapsible and expandable introducer sheath.
Figure 17:
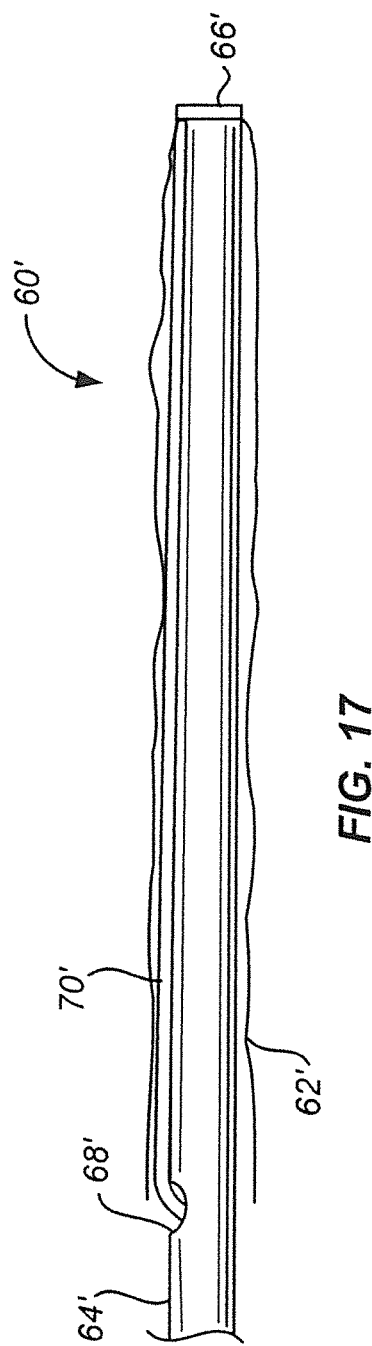
FIG. 17 is a cross-sectional side view of another embodiment of the present radially collapsible and expandable thrombus collection device.

In an alternative embodiment of the sheath 20', the sheath wire 38' may not be coiled around the inner layer 32' when the sheath 20' is in the collapsed state. For example, FIG. 16 shows an alternative sheath 20' in which the sheath wire 38' extends substantially straight from the opening 50' to the distal end 42' of the sheath casing 30'. Similarly, in an alternative embodiment of the thrombus collection device 60', the device wire 70' may not be coiled around the catheter 64' when the device casing 62' is in the collapsed state. For example, FIG. 17 shows an alternative thrombus collection device 60' in which the device wire 70' extends substantially straight along the catheter 64' from the opening 68' to the distal end 66' of the catheter 64'. In both embodiments of FIGS. 16 and 17, the wire 38', 70' coils around the inner layer 32'/catheter 64' in response to a distally directed force applied to the wire 38', 70', substantially as described above with respect to the foregoing embodiments.

As illustrated above, the present embodiments of the radially collapsible and expandable sheath 20 advantageously provide an introducer sheath that can be adjusted to accommodate intravascular devices of various sizes. The sheath 20 is simple in construction, including only two pieces (the casing 30 and the wire 38) in certain embodiments. The sheath 20 is easily adjustable in radial dimension through the application of pushing or pulling force to the wire 38. The sheath 20 can expand radially on its own in response to movement of a large object into the sheath, such as a large intravascular device or a device carrying a relatively large amount of thrombus. In the latter case, this property of the sheath facilitates removal of large thrombi without need for macerating the thrombi or treating them with a thrombolytic agent before moving them through the sheath. The sheath 20 can be expanded within the vasculature to radially expand the vasculature. When collapsed, the portion of the sheath 20 extending through the percutaneous access opening promotes hemostasis by allowing the opening to partially or completely collapse.

As also illustrated above, the present embodiments of the radially collapsible and expandable thrombus collection device 60 advantageously provide a collection device that can be collapsed to a low profile for easy introduction to the vasculature through a sheath, and easy penetration of the thrombus. When the collapsed device 60 is advanced past the thrombus, it can be expanded to match the interior diameter of the vasculature and pulled back to entrain the thrombus. It is optional to macerate the thrombus or to soften it with a thrombolytic prior to extraction. The proximal opening of the casing, supported by the wire, simply pulls the thrombus away from the vasculature wall and traps it within the casing. This embodiment is particularly useful for removing thrombi that repeatedly form in arterio-venous fistulas (AVF) of hemodialysis patients. The thrombus collection device 60 enables removal of the thrombi without the need for repeated surgical cut downs. Several devices 60 can be provided in a package or kit for use within a single procedure, e.g. when thrombus is to be removed in several stages each calling for a separate device 60.

As also illustrated above, the present embodiments of the radially collapsible and expandable sheath 20 can be combined with the present embodiments of the radially collapsible and expandable thrombus collection device 60 to form a system 88 (FIG. 11) for performing a thrombectomy. The system 88 achieves the combined advantages of each component of the system 88. Those of ordinary skill in the art will appreciate, however, that both the sheath 20 and the thrombus collection device 60 are usable separately.

Figure 18:
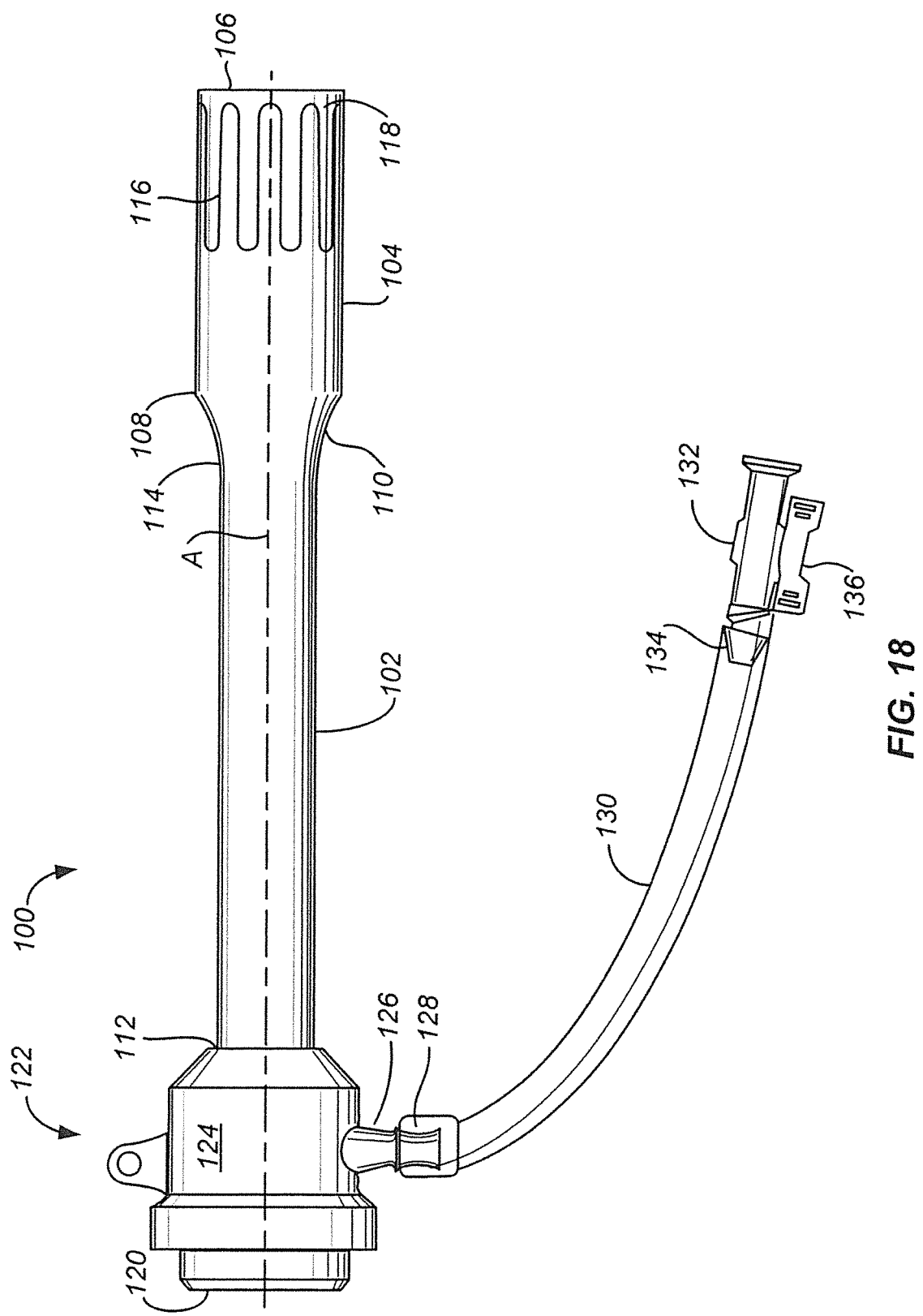
FIG. 18 is a side elevation view of another embodiment of the present introducer sheath.

FIG. 18 illustrates another embodiment of the present introducer sheaths. The sheath 100 is tubular, and includes a medial neck portion 102. At a distal end, the neck portion 102 flares outwardly to a wider bell portion 104. The distal end 106 of the bell portion 104 is open.

The neck portion 102 and the bell portion 104 may comprise a compliant material. As used herein, the term compliant should be understood to include at least the following properties: flexibility, elasticity, and collapsibility/expandability. Further, because the sheath 100 is configured for use internally, the material is preferably biocompatible. Example materials for the sheath 100 include silicone film, polyisoprene, TECOTHANE®, PELLETHANE®, and other materials having similar properties. The compliant sheath material is advantageously kink resistant and capable of folding upon itself.

In one embodiment, the sheath 100 comprises HT-310 synthetic polyisoprene having a thickness of approximately 3-4.5 mils. A length of the bell portion 104 is approximately 26 mm, as measured from the distal end 106 to the transition point 108 between the bell portion 104 and the flared portion 110. A diameter of the bell portion 104 is approximately 10 mm. A length of the neck portion 102 is approximately 34 mm, as measured from the proximal end 112 to the transition point 114 between the neck portion 102 and the flared portion 110. A diameter of the neck portion 102 is approximately 7 mm. A length of the flared portion 110 is approximately 10 mm. The foregoing material and dimensions are merely one example, and are not limiting.

The bell portion 104 of the sheath 100 includes a wire 116 that is encased within the compliant material. Unlike the sheath 20 described above and illustrated in FIGS. 1-6, the wire 116 is not movable relative to the compliant sheath material. The sheath 100 may, for example, be made by overmolding the compliant sheath material over the wire 116. The resulting structure keeps the wire 116 in the desired position along the length of the bell portion 104.

The wire 116 extends around the circumference of the bell portion 104 along a path that repeatedly doubles back and forth in the direction of the longitudinal axis A of the sheath 100. As measured in the direction of the longitudinal axis A, the wire 116 extends over approximately half the length of the bell portion 104 from the distal end 106 thereof to approximately the center thereof. As illustrated, however, a narrow band 118 of the bell portion 104 extends beyond the wire 116 at the distal end 106. A length of this band 118, as measured in the direction of the longitudinal axis A, may be approximately 1 mm in one embodiment.

The wire 116 supports the compliant material, maintaining the bell portion 104 in its expanded shape when the sheath 100 is unstressed. The wire 116 comprises a material that is flexible but incompressible. Further, because the wire 116 is configured for use internally, the material is preferably biocompatible. Example materials for the wire 116 include nickel-titanium (NiTi) alloys, stainless steel, polyether ether ketone (PEEK) and other materials having similar properties.

At a proximal end 120, the sheath 100 includes a flush port 122. The flush port 122 includes a tubular portion 124 that is coaxial with the neck portion 102 and the bell portion 104. Together, the tubular portion 124, the neck portion 102 and the bell portion 104 define an interior lumen, or sheath lumen (not shown). A port 126 extends radially from the tubular portion 124. The port 126 defines a port lumen (not shown) that is in fluid communication with the sheath lumen. The port 126 is conically shaped, tapering down to a smaller diameter with increasing distance from the tubular portion 124. A medial portion of the port 126 includes an annular bulge 128 where the exterior diameter of the port 126 is increased. The port 126 is configured to receive standard medical tubing 130 in a liquid tight friction fit with the tubing 130 extending around the outside of the bulge 128. An end of the tubing 130 spaced from the port 126 includes a connector 132. In the illustrated embodiment, the illustrated connector 132 is a female Luer connector 132. A conical distal end 134 of the connector 132 is received within the tubing 130 in a liquid tight friction fit. The connector 132 includes a stopcock 136 that enables flow through the connector 132 to be selectively blocked. The flush port 122 enables fluid to be injected and/or aspirated from the sheath lumen. For example, a syringe (not shown) may be connected to the connector 132, and fluid may be injected or aspirated by depressing or drawing back on the syringe plunger.

The introducer sheath 100 of FIG. 18 is configured for passage into a patient's vasculature (e.g. in a vein or artery, an arterio-venous fistula (AVF) or arterio-venous graft (AVG), or alternatively in a non-vascular location such as the peritoneal cavity or other bodily cavities or hollow anatomical structures) through an opening at a percutaneous access site. Once deployed, the sheath 100 can be used as a conduit for introducing one or more intravascular devices into the patient's vasculature. For example, and as discussed further below, in one embodiment the sheath 100 can be used to introduce a thrombectomy device. FIG. 18 illustrates the introducer sheath 100 in an unstressed, or expanded, configuration. The compliant portions of the introducer sheath 100 are configured to be radially compressed for ease of introduction into the vasculature, as described below. Once deployed within the vasculature, a hemostasis valve 138 at the proximal end of the sheath 100 (FIG. 20) resists outflow of bodily fluids through the sheath 100. The hemostasis valve 138 is shaped substantially as a disk, and is located within the tubular portion 124 at the proximal end 120 thereof. The valve 138 may, for example, comprise a foam material. The valve 138 forms a seal around the exterior of a tubular dilator 140, which is described below.

Figure 19:
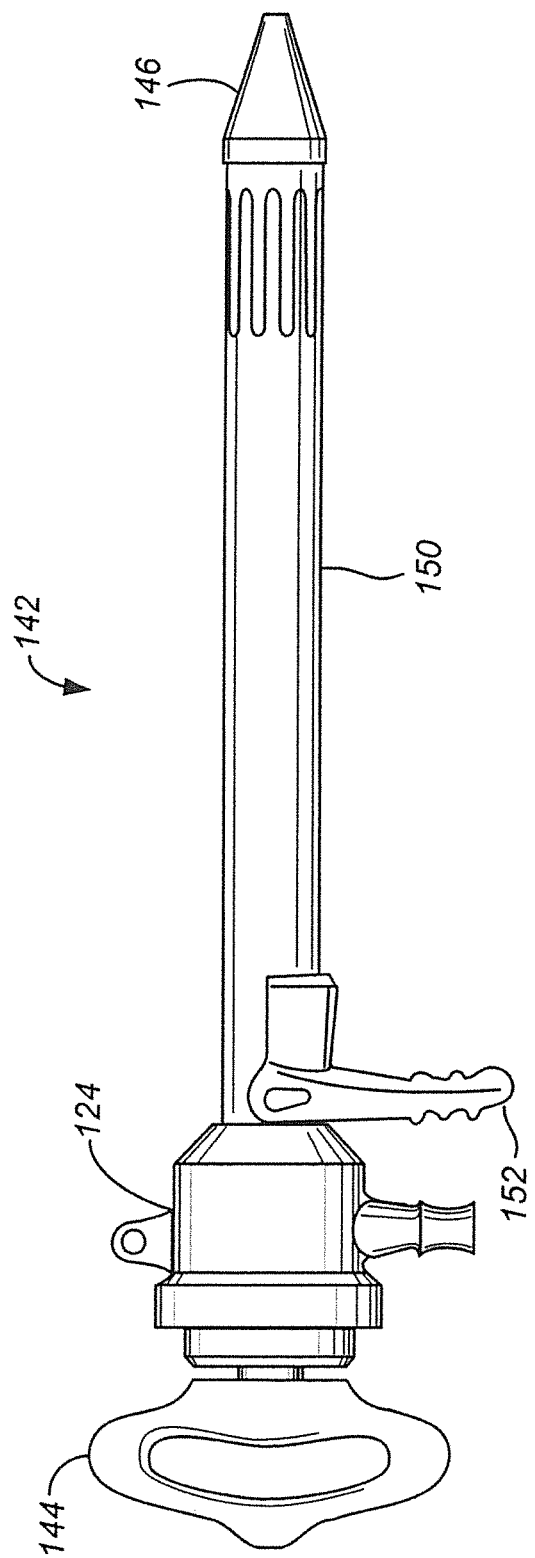
FIG. 19 is a side elevation view of one embodiment of a deployment apparatus for the introducer sheath of FIG. 18.
Figure 20:
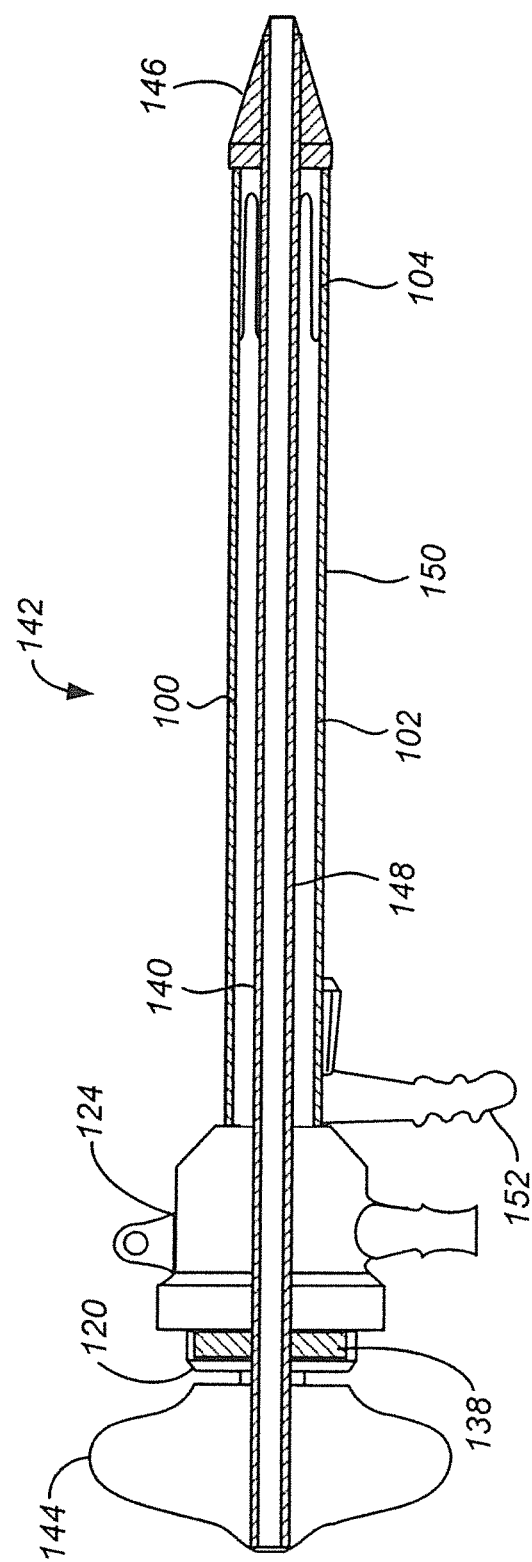
FIG. 20 is a side cross-sectional view of the deployment apparatus of FIG. 19.

FIGS. 19 and 20 illustrate one embodiment of a deployment apparatus 142 for the introducer sheath 100 of FIG. 18. With reference to the cross-sectional view of FIG. 20, the deployment apparatus 142 includes a tubular dilator 140, which may also be referred to as a hypotube 140. The dilator 140 is a rigid or semi-rigid component configured to guide the deployment apparatus 142 through a skin puncture and through the vasculature, as described in further detail below. The dilator 140 includes a proximal handle 144, a conically shaped distal tip 146, and defines a lumen 148 that extends between the proximal and distal ends. The handle 144 is shaped as a round knob. The lumen 148 extends through the handle 144 and through the distal tip 146. The lumen is configured to receive a guide wire (not shown) to facilitate introduction of the dilator 140 into a patient, as described in detail below.

With continued reference to FIG. 20, the introducer sheath 100 of FIG. 18 is disposed coaxially about the outside of the dilator 140, and an outer sheath 150 is disposed coaxially about the outside of the introducer sheath 100. The outer sheath 150 has an inner diameter that is approximately equal to an outer diameter of the neck portion 102 of the introducer sheath 100, but less than the outer diameter of the bell portion 104 of the introducer sheath 100. The outer sheath 150 thus radially compresses the bell portion 104, which facilitates introduction of the sheath 100 into the patient. In certain embodiments, the outer sheath 150 comprises a non-elastic material so that the radially compressed bell portion 104 does not induce expansion of the outer sheath 150.

The outer sheath 150, however, is a tearaway sheath. Thus, it comprises a material that can be torn by hand. Example materials include polytetrafluoroethylene (PTFE) and materials having similar properties. The outer sheath 150 includes a proximal handle 152 that extends radially away from the outer sheath 150 at a location just distal of the tubular portion 124 of the introducer sheath 100. As discussed further below, the operator may remove the outer sheath 150 by grasping the handle 152 and pulling it proximally while holding the introducer sheath 100 and the dilator 140 steady. The outer sheath 150 material tears away from the deployment apparatus 142 as it is withdrawn from the percutaneous access site. Once the outer sheath 150 is removed, the bell portion 104 of the introducer sheath 100 expands to its unstressed condition, subject to any stresses applied by the patient's vasculature.

Figure 21:
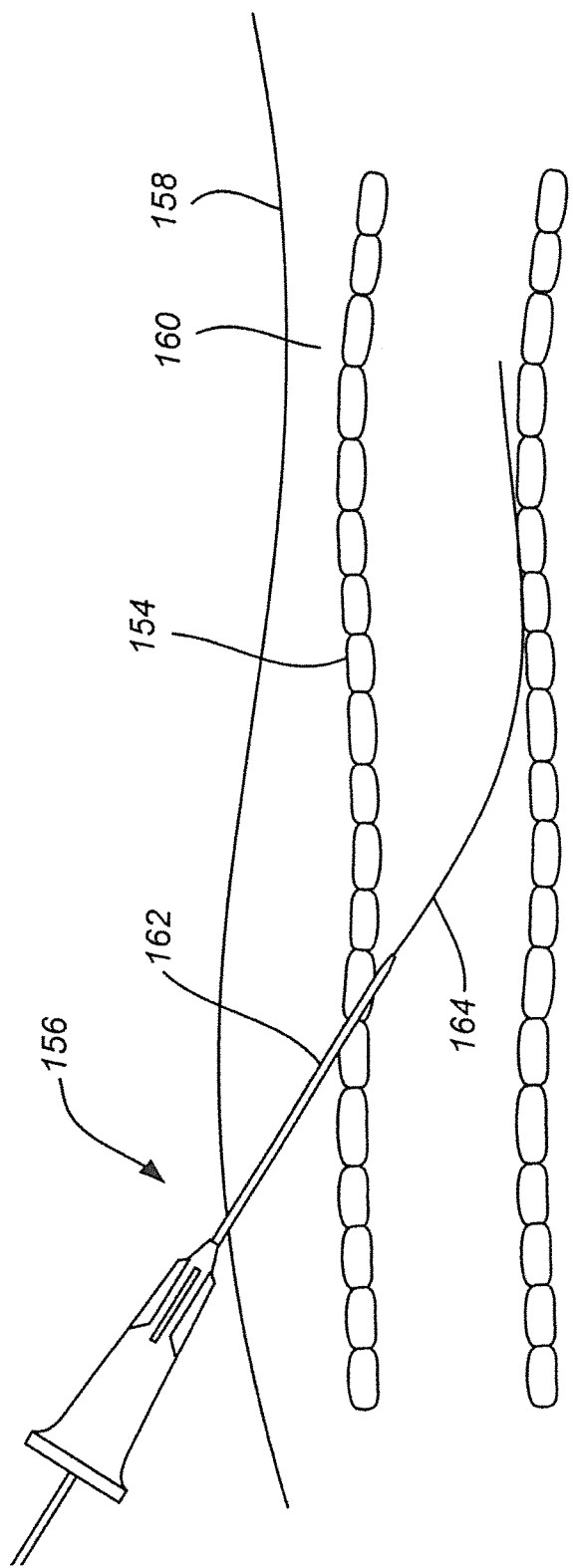
FIGS. 21-24 are side elevation views of one embodiment of steps for deploying the introducer sheath of FIG. 18 in a patient's vasculature at a percutaneous access site.

FIGS. 21-24 illustrate one embodiment of a method for deploying the introducer sheath 100 of FIG. 18 in a patient's vasculature 154 at a percutaneous access site 156 using the deployment apparatus 142 of FIGS. 19 and 20. The access site 156 may be prepared by puncturing the skin 158, any underlying tissue 160, and the vasculature 154 with a needle 162, as shown in FIG. 21. The operator then introduces a guide wire 164 through the lumen of the needle 162, and withdraws the needle 162.

Figure 22:
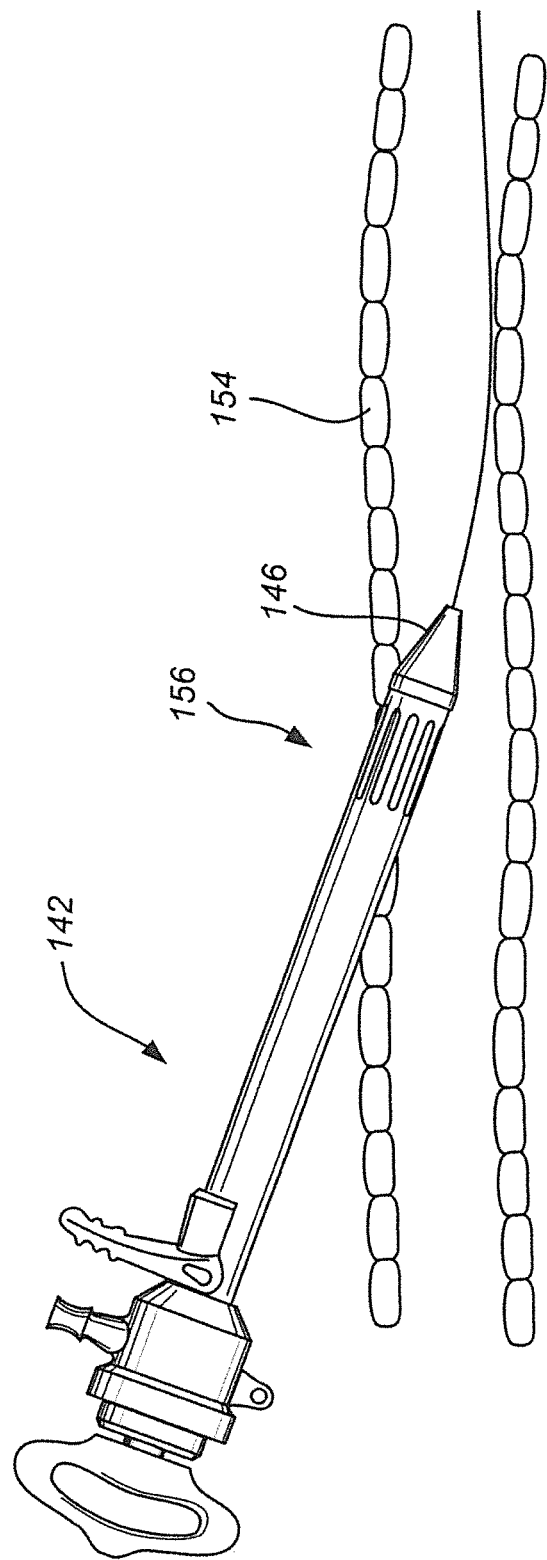

With reference to FIG. 22, the operator introduces the deployment apparatus 142 into the vasculature 154 through the puncture site 156 using the guide wire 164. The operator threads the guide wire 164 into the dilator lumen 148 (FIG. 20) from the distal end 146 and advances the deployment apparatus 142 through the puncture site 156. In some embodiments the dilator 140 is a rigid component that provides sufficient column strength to facilitate tissue puncturing and/or penetration. However, in alternative embodiments the dilator 140 includes sufficient flexibility to facilitate navigating tortuous vasculature 154. The conically shaped distal tip 146 of the dilator 140 facilitates passage of the deployment apparatus 142 through the patient's tissue 160 (FIG. 21) and into the vasculature 154.

Figure 23:
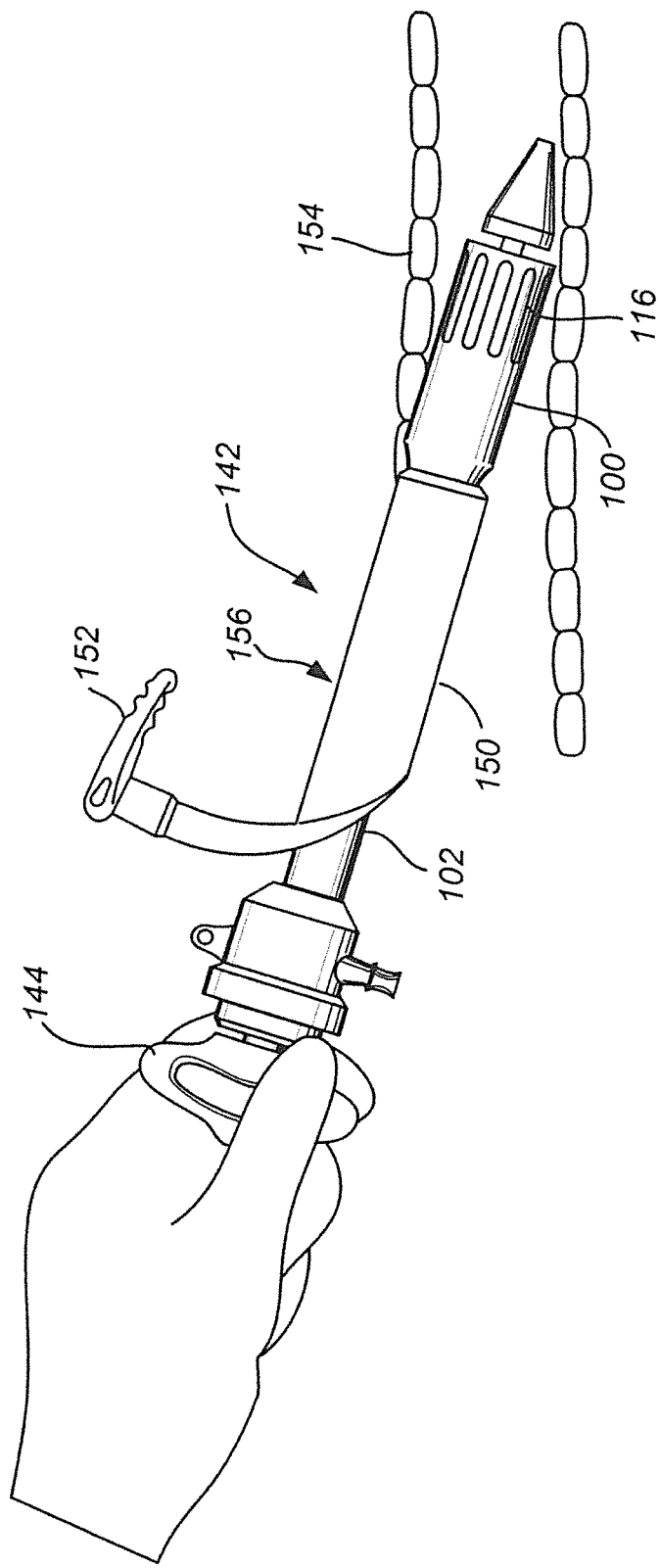

With reference to FIGS. 22 and 23, after penetrating the vasculature 154 the deployment apparatus 142 is advanced through the vasculature 154 until the handle portion 152 of the outer sheath 150 approaches the puncture site 156. In this position, the introducer sheath 100 is located such that the bell portion 104 is located entirely within the vasculature 154 and the neck portion 102 traverses the puncture site 156. The hemostasis valve 138 (FIG. 20) within the introducer sheath 100 resists outflow of blood through the annular space defined by the interior of the sheath 100 and the exterior of the dilator 140. The dilator 140 may also include a hemostasis valve (not shown) to resist outflow of blood through the dilator lumen 148.

With reference to FIG. 23, the operator next removes the outer sheath 150 from the deployment apparatus 142. As indicated above, the outer sheath 150 is a tearaway sheath. Thus, to remove the outer sheath 150, the operator grasps the handle 152 and pulls it proximally while holding the introducer sheath 100 and the dilator 140 steady. The operator may, for example, grasp the outer sheath handle 152 with one hand and the dilator handle 144 with the other hand. The outer sheath 150 tears away from the remainder of the deployment apparatus 142 and pulls through the puncture site 156.

Figure 24:
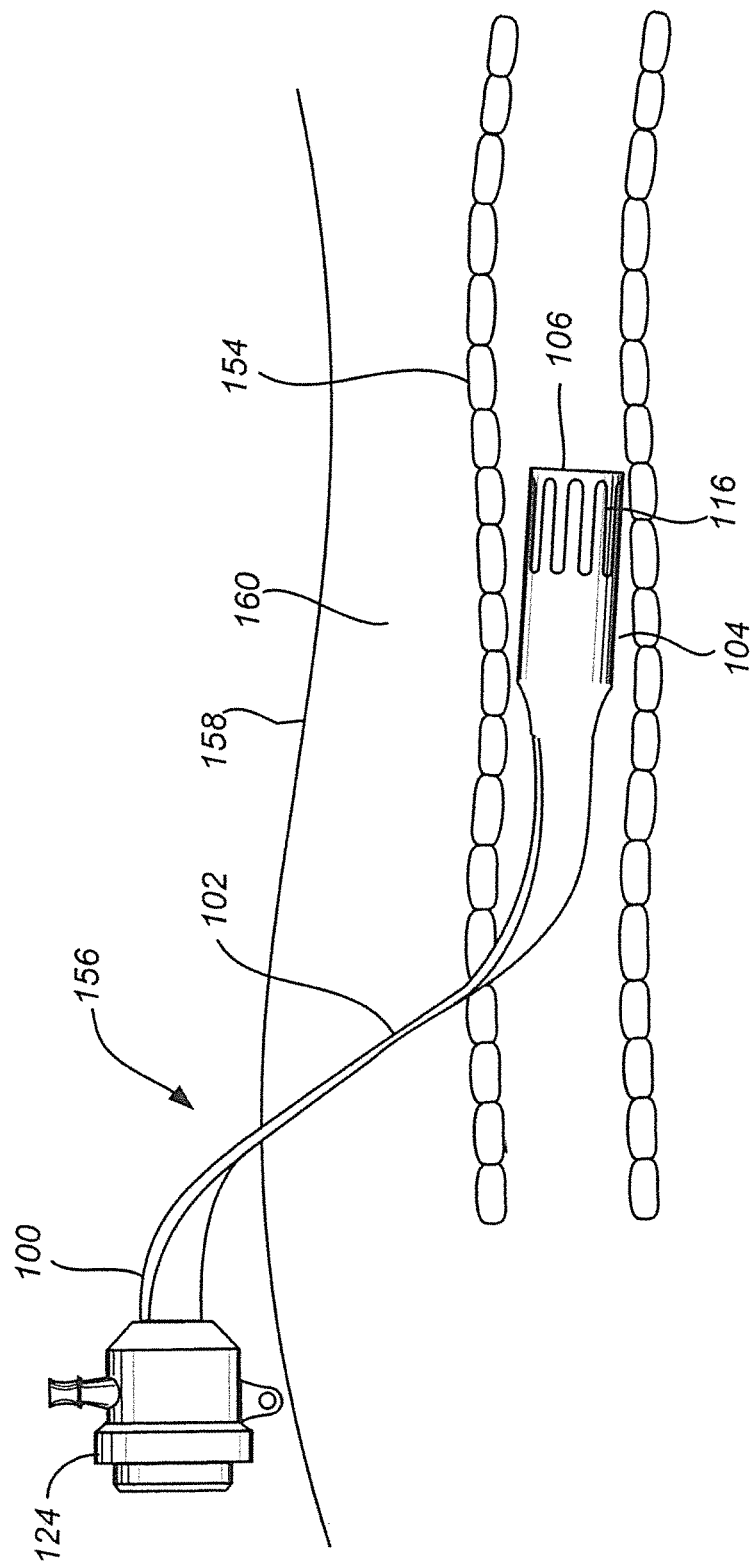

With reference to FIGS. 23 and 24, the operator draws the entire outer sheath 150 out of the body through the puncture site 156. Upon removal of the outer sheath 150, the compressive force applied to the introducer sheath 100 by the outer sheath 150 is no longer present. The bell portion 104 of the introducer sheath 100 thus expands as the stored energy in the wire 116 is released. FIG. 24 illustrates the introducer sheath 100 in its expanded state within the vasculature 154. Depending upon the relative dimensions of the introducer sheath 100 and the vasculature 154, the vasculature 154 may constrain the expansion of the introducer sheath 100 somewhat so that it does not achieve the fully relaxed state that it would outside the body. Skin 158 and underlying tissue 160 further constrain expansion of the neck portion 102 where it traverses the puncture site 156.

With reference to FIGS. 23 and 24, after removing the outer sheath 150 the operator next removes the dilator 140. To remove the dilator 140, the operator draws back on the proximal handle 144. During withdrawal, the operator may optionally apply digital pressure at the puncture site 156 in order to prevent the introducer sheath 100 from being withdrawn together with the dilator 140 due to friction between those two components where they are squeezed by the elastic skin 158 at the puncture site 156. With the dilator 140 completely removed, the introducer sheath 100 is disposed within the vasculature 154 through the puncture site 156 as shown in FIG. 24. The tubular portion 124 is disposed exteriorly of the body, the bell portion 104 is disposed within the vasculature 154, and the neck portion 102 traverses the skin 158 and tissue 160 therebetween. Advantageously, the compliant nature of the neck portion 102 promotes hemostasis at the puncture site 156 by allowing the elastic skin 158 to collapse around the puncture. The compliant neck 102 further speeds hemostasis at the end of a procedure, because the skin 158 and underlying tissue 160 do not remain stretched for an extended period. The hemostasis valve 138 within the proximal end 120 of the introducer sheath 100 (FIG. 20) further promotes hemostasis at the puncture site 156. When the dilator 140 is withdrawn, the hemostasis valve 138 may close to seal the opening formerly occupied by the dilator 140. The valve 138 may reopen as additional apparatus is introduced into the vasculature 154 through the sheath 100. However, the valve 138 preferably forms a seal around any such apparatus.

The introducer sheath 100 described above may advantageously be used to introduce a wide variety of instruments into a patient's vasculature 154. For example, the introducer sheath 100 may be used to introduce a thrombus collection device. Various examples of thrombus collection procedures using the present embodiments are described below.

Figure 25:
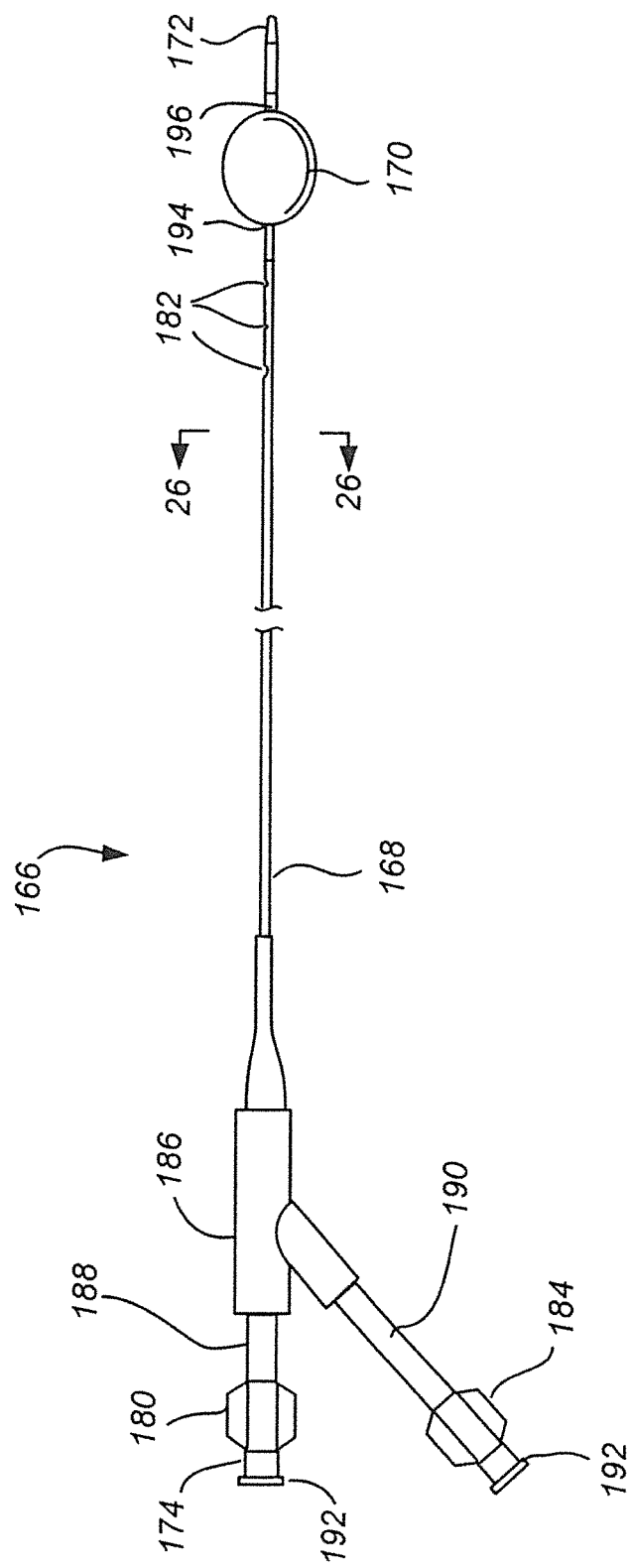
FIG. 25 is a side elevation view of one embodiment of the present thrombus collection device having aspiration ports.
Figure 26:
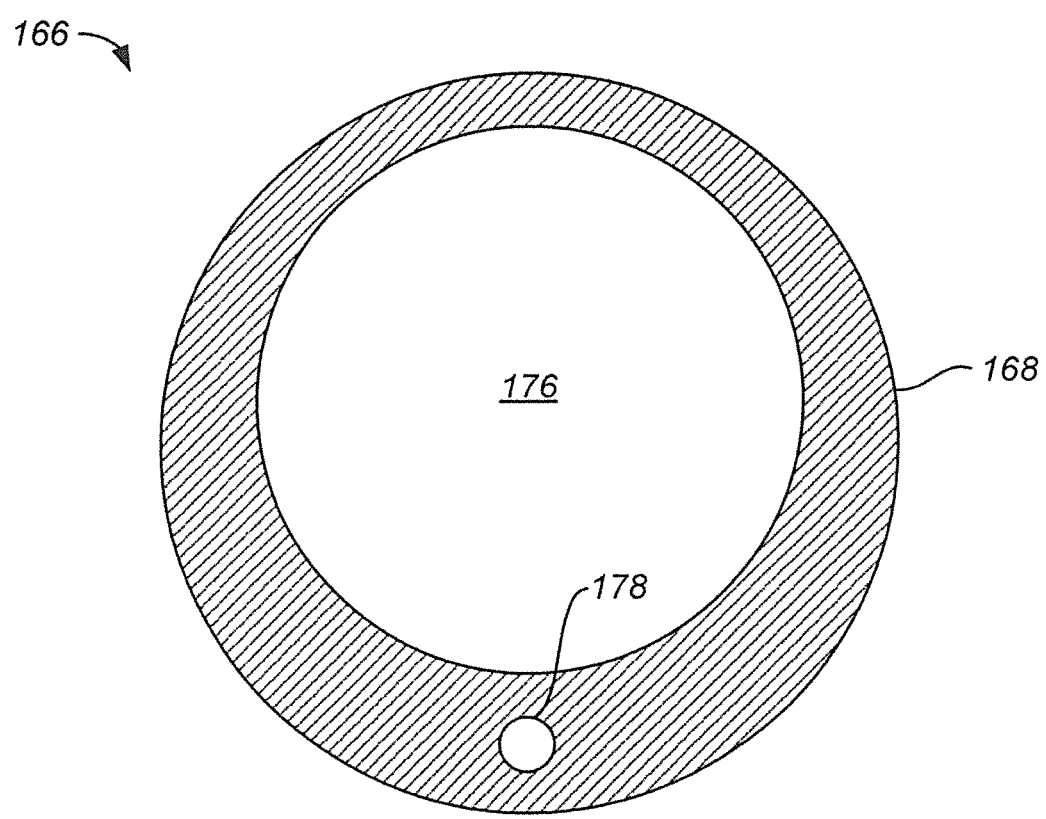
FIG. 26 is a cross-sectional end view of the thrombus collection device of FIG. 25, taken along the line 26-26 in FIG. 25.

FIGS. 25 and 26 illustrate an aspiration catheter 166, which is another embodiment of the present thrombus collection devices. With reference to FIG. 25, the catheter 166 includes an elongate body 168 having a balloon 170 at its distal end 172. The catheter body 168 comprises a flexible material that is configured for navigating tortuous vasculature. However, the catheter body 168 material includes sufficient rigidity to facilitate guiding the catheter 166 through the vasculature from the proximal end 174. Example materials for the catheter body 168 include polyether block amide (PEBAX®) and materials having similar properties.

FIG. 26 illustrates a cross-sectional view of the catheter body 168. The body 168 defines two radially spaced lumens 176, 178 that are not in fluid communication with one another. The first lumen 176 is an aspiration lumen 176 that extends from an aspiration connector 180 (FIG. 25) at the proximal end 174 of the catheter 166 to a plurality of aspiration openings 182 toward the distal end 172 of the catheter 166. The second lumen 178 is an inflation lumen 178 that extends from an inflation connector 184 at the proximal end 174 of the catheter 166 to the balloon 170 toward the distal end 172 of the catheter 166. The aspiration lumen 176 has a larger diameter than the inflation lumen 178, and is configured for passage of thrombus, as described below. In one embodiment, the catheter body 168 may have a diameter of 6 Fr, while the aspiration lumen 176 may have a diameter of 0.055".

In certain embodiments, the aspiration lumen 176 may further extend to the distal end 172, which is open but sealed by a valve (not shown). The valve enables a guide wire (not shown) to pass to facilitate introduction of the catheter 166 into the vasculature. However, upon withdrawal of the guide wire the valve seals to resist flow into or out of the distal end 172 of the aspiration lumen 176.

With reference to FIG. 25, the aspiration connector 180 and the inflation connector 184 extend proximally from a Y-shaped body 186. The body 186 includes a main conduit 188 that extends inline with the catheter body 168. The aspiration connector 180 extends proximally from the main conduit 188, inline therewith. The body 186 further includes a branch conduit 190 that extends at an angle from the body 186. The inflation connector 184 extends proximally from the branch conduit 190, inline therewith. In the illustrated embodiment, both connectors 180, 184 comprise a female Luer connector including an external thread 192. In alternative embodiments different types of connectors could be substituted. In certain embodiments, either or both of the connectors 180, 184 may include a stopcock (not shown) for selectively halting liquid flow through the connector(s) 180, 184.

The Y-shaped body 186 and the connectors 180, 184 may be formed as a single piece or as multiple pieces. These portions are preferably formed from a rigid medical grade plastic. For example, these portions may comprise polycarbonate, acrylic, polypropylene, styrene, or any other suitable plastic material.

With continued reference to FIG. 25, and as indicated above, the aspiration catheter 166 includes a plurality of aspiration openings 182 toward the distal end 172. Three openings are shown, but other embodiments may include any number of openings 182, including only a single opening 182. The aspiration openings 182 are in fluid communication with the aspiration connector 180 through the aspiration lumen 176. During a thrombus collection procedure, a syringe (not shown) may be connected to the aspiration connector 180. Drawing back upon a plunger of the syringe creates suction at the aspiration openings 182. The suction can be used to draw pieces of the thrombus into the aspiration lumen 176 for removal from the vasculature. This process is described more fully below.

The aspiration catheter 166 further includes a balloon 170 toward the distal end 172. The balloon 170 is shown in a partially inflated state for illustration. The balloon 170 is sealed at its proximal end 194 and distal end 196 to the catheter body 168. An inflation port (not shown) passes through the wall of the catheter body 168 within the balloon 170. The interior of the balloon 170 is in fluid communication with the inflation lumen 178 through the inflation port. During a thrombus collection procedure, a syringe (not shown) may be connected to the inflation connector 184. The balloon 170 may be inflated by depressing the syringe plunger to force a fluid through the inflation lumen 178 and into the balloon 170. The balloon 170 may be deflated by drawing the syringe plunger back to evacuate the fluid from the balloon 170. For intravascular procedures, the inflation fluid is preferably a non-toxic liquid, such as saline. Thus, as used herein the terms inflate and deflate are to be construed broadly enough to include using a liquid as the inflation agent.

Figure 27:
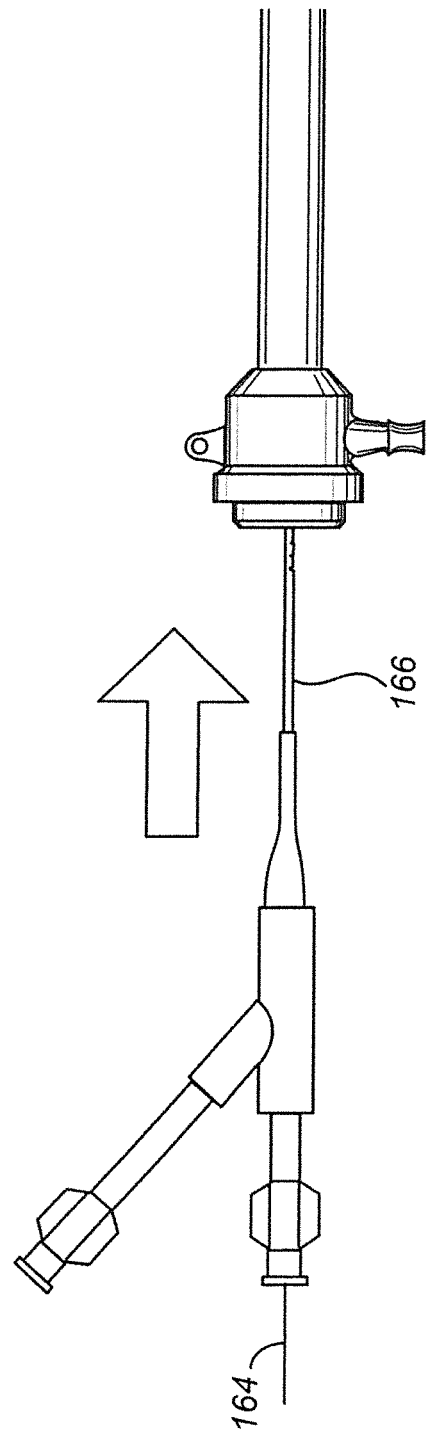
FIGS. 27 and 28 are side elevation views of the proximal portions and distal portions, respectively, of the introducer sheath of FIG. 18 and the thrombus collection device of FIG. 25 during one step of a percutaneous thrombus collection procedure.
Figure 28:
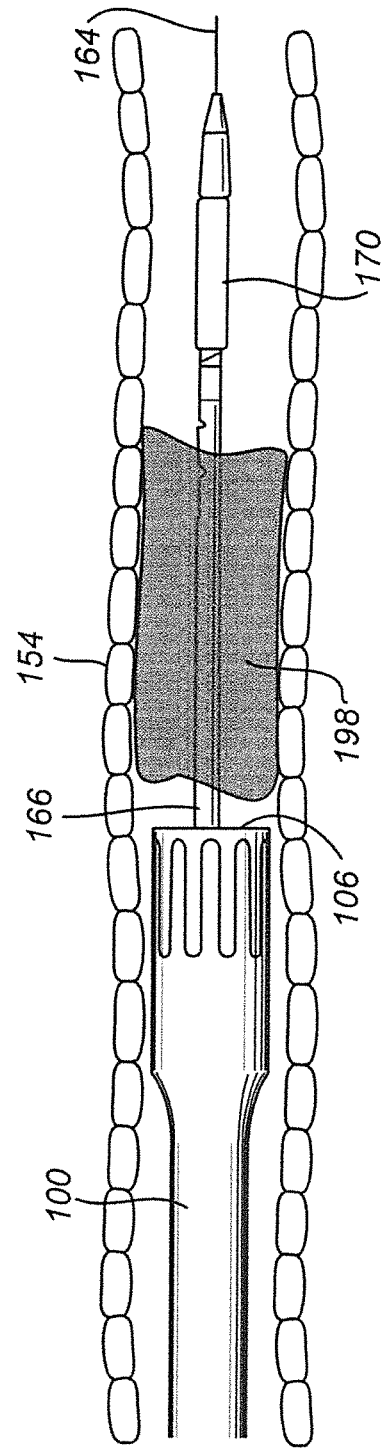
Figure 29:
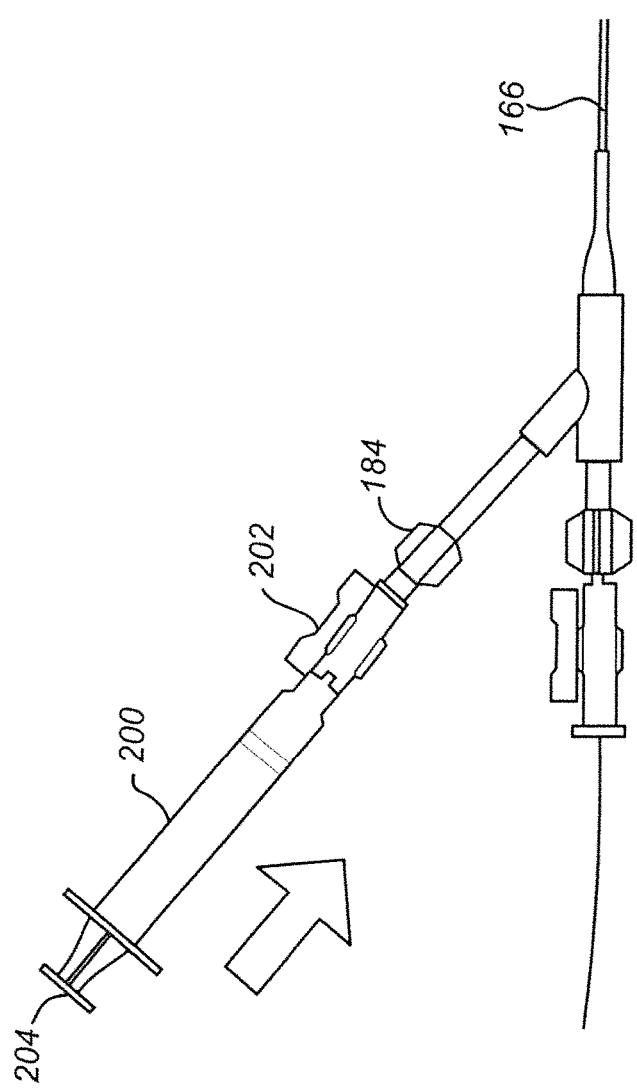
FIGS. 29 and 30 are side elevation views of the proximal portions and distal portions, respectively, of the introducer sheath of FIG. 18 and the thrombus collection device of FIG. 25 during another step of a percutaneous thrombus collection procedure.
Figure 30:
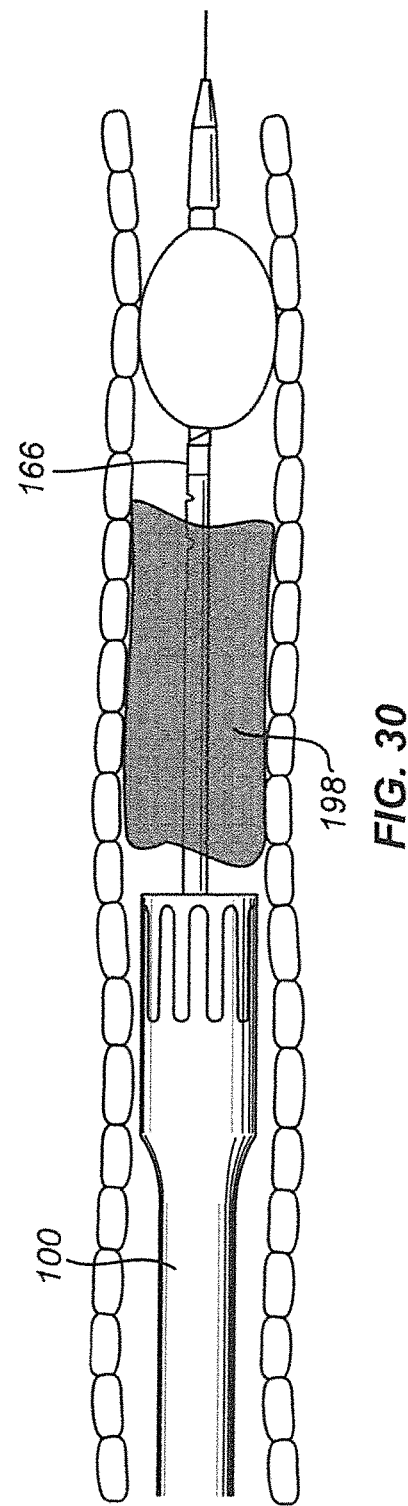

As described above, the aspiration catheter 166 shown in FIGS. 25 and 26 is configured for percutaneously removing a thrombus from a patient's vasculature. FIGS. 27-35 illustrate one example of such a procedure. In FIGS. 27-34, each drawing sheet illustrates the proximal portions (odd numbered figures) of the introducer sheath 100 and the aspiration catheter 166 and the distal portions (even numbered figures) as they appear during the same step of the procedure. In other words, FIGS. 27 and 28 illustrate different portions of the apparatus during the same step of the procedure, FIGS. 29 and 30 illustrate different portions of the apparatus during a subsequent step of the procedure, etc.

With reference to FIGS. 27 and 28, the aspiration catheter 166 is introduced into the vasculature 154 through the introducer sheath 100 described above with respect to FIGS. 18-24. The introducer sheath 100 may be deployed according to the method described above with respect to FIGS. 21-24. The aspiration catheter 166 is then advanced distally through the sheath 100, the vasculature 154, and the thrombus 198 until the balloon 170 is disposed on the far side of the thrombus 198 (FIG. 28). A guide wire 164 extending through the aspiration lumen 176 may be used to advance the catheter 166. As shown, the catheter 166 is advanced with the balloon 170 in the deflated state for ease of passage through the sheath 100, the vasculature 154 and the thrombus 198. The conically shaped distal tip 172 further facilitates passage of the catheter 166, especially through the constricted portion of the sheath 100 that traverses the puncture site, and through the thrombus 198.

With reference to FIGS. 29 and 30, when the catheter 166 has advanced sufficiently that the balloon 170 is disposed on the far side of the thrombus 198, the operator connects a syringe 200 (FIG. 29) filled with inflation liquid to the inflation connector 184. As shown, a Luer stopcock 202 may be connected between the syringe 200 and the inflation connector 184. The operator depresses the syringe plunger 204 to force the inflation liquid into the balloon 170 through the inflation lumen 178. The operator inflates the balloon 170 until it presses against the interior walls of the vasculature 154 on the far side of the thrombus 198 (FIG. 30). If the stopcock 202 is not provided, the operator maintains the syringe 200 connected to the inflation connector 184 in order to maintain the inflation pressure within the balloon 170. However, if the stopcock 202 is provided, the operator moves the stopcock 202 to a position to prevent liquid flow through the inflation connector 184. The operator may then disconnect the syringe 200 from the stopcock 202, which may make it easier for the operator to perform subsequent steps of the procedure.

Figure 31:
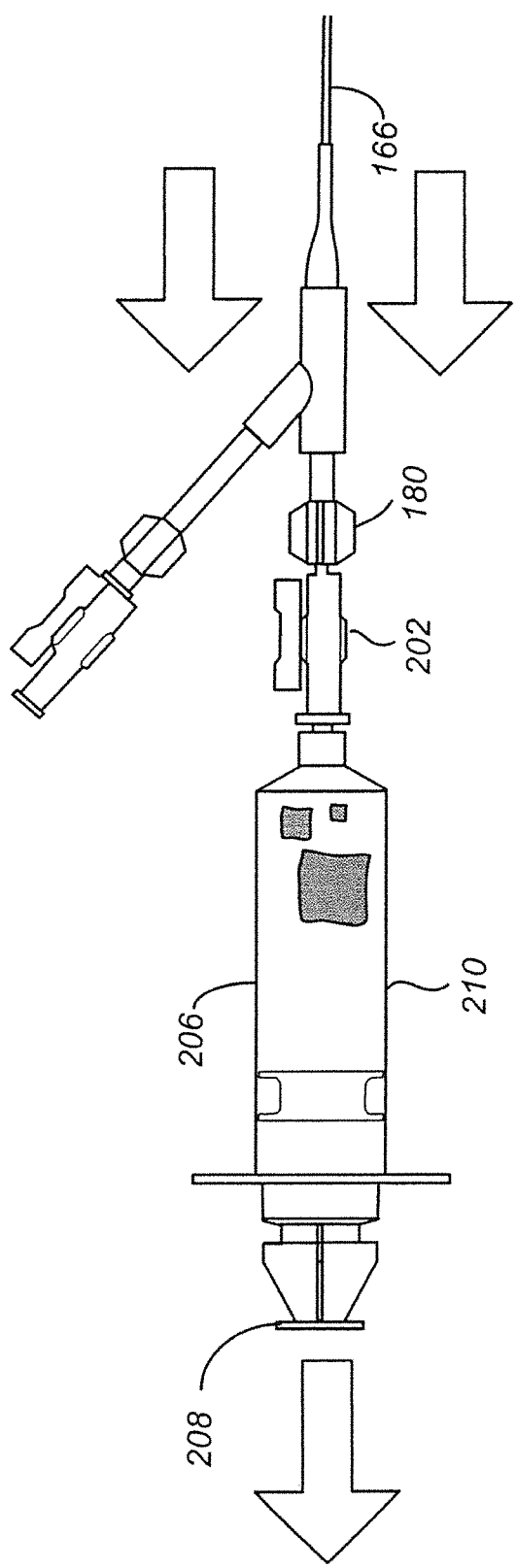
FIGS. 31 and 32 are side elevation views of the proximal portions and distal portions, respectively, of the introducer sheath of FIG. 18 and the thrombus collection device of FIG. 25 during another step of a percutaneous thrombus collection procedure.
Figure 32:
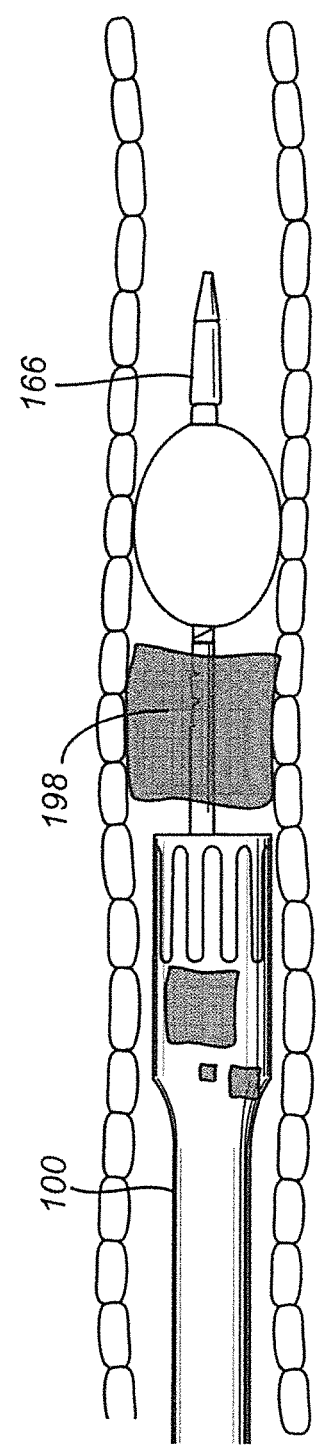

With reference to FIGS. 31 and 32, the operator removes the thrombus 198 from the vasculature 154 by using a combination of suction through the aspiration openings 182, and proximal movement of the inflated balloon 170 across the thrombus 198. These actions may occur simultaneously, or in succession, or alternatingly. The following discussion describes a method for applying suction simultaneously while drawing the inflated balloon 170 across the thrombus 198. This illustrated method is only one of many possibilities for removing the thrombus 198, and is not intended to be limiting.

With reference to FIG. 31, the operator connects a Luer stopcock 202 to the aspiration connector 180 and an empty syringe 206 to the stopcock 202. If a guide wire 164 was used to advance the catheter 166, it is removed prior to connection of the syringe 206. The syringe 206 is configured so that the plunger 208 can be drawn back to create a vacuum within the barrel 210 and the plunger 208 locked to maintain the vacuum. One such syringe is sold under the trade name VACLOK®. To generate suction, the operator draws back on the syringe plunger 208 with the stopcock 202 in the closed position and then locks the plunger 208. The operator then draws the catheter 166 out of the vasculature 154 while simultaneously moving the stopcock 202 to the open position. Moving the stopcock 202 to the open position exposes the vacuum in the syringe barrel 210 to the aspiration lumen 178, generating suction that pulls pieces of the thrombus 198 into the aspiration lumen 176 through the aspiration openings 182. The aspiration openings 182 thus advantageously assist in collecting the thrombus 198 both by tearing away pieces of thrombus 198 from the larger whole, and by vacuuming up any loose pieces of thrombus 198. Some of these pieces of thrombus 198 may be sucked into the syringe 206, as shown in FIG. 31.

Because the operator draws the catheter 166 out of the vasculature 154 simultaneously while generating suction at the aspiration openings 182, the aspiration openings 182 are more likely to be exposed to all portions of the thrombus 198 as the openings 182 are drawn across the thrombus 198, as shown in FIG. 32. The suction is thus more likely to remove more of the thrombus 198 than if the catheter 166 remains stationary while the vacuum is applied. In certain embodiments, the aspiration openings 182 may be located within the thrombus 198 at the point in the procedure where the operator opens the stopcock 202. In alternative embodiments, some or all of the openings 182 may be disposed proximally and/or distally of the thrombus 198 at this point in the procedure.

In addition to the vacuum action, pulling back on the aspiration catheter 166 pulls the balloon 170 against the distal side of the thrombus 198, as shown in FIG. 32. The balloon 170, which fills the circumference of the vasculature 154, pulls the thrombus 198 away from the vasculature 154. Portions of the thrombus 198 that are not sucked into the aspiration lumen 176 are drawn into the sheath 100 by the balloon 170.

Figure 33:
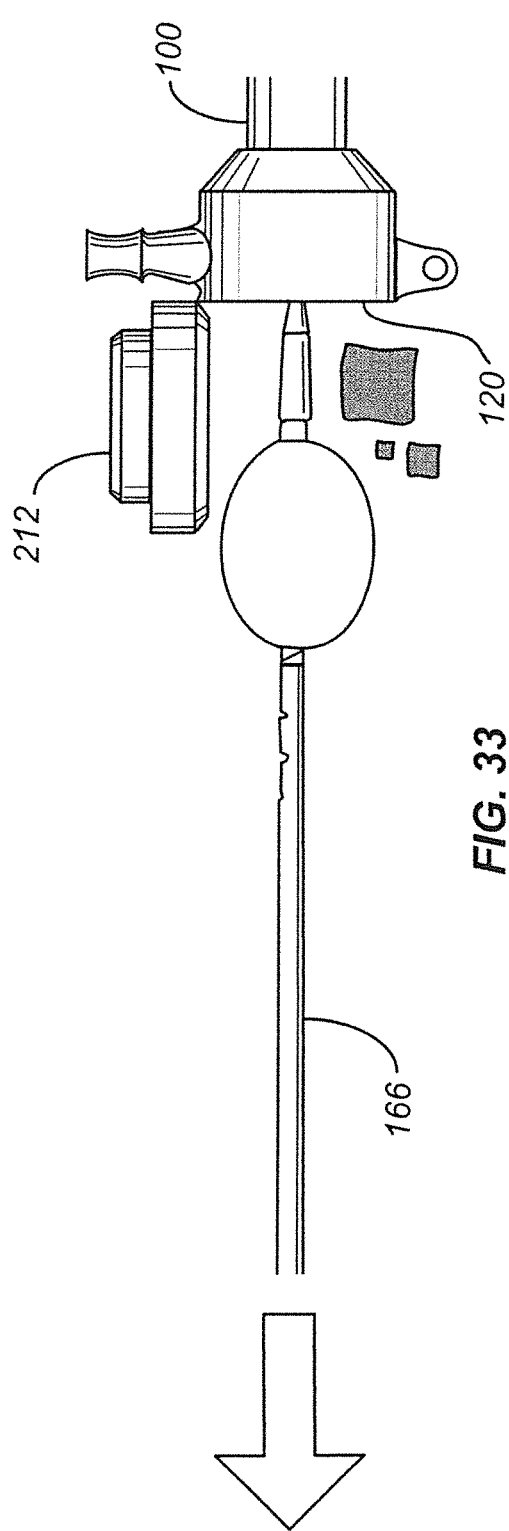
FIGS. 33 and 34 are side elevation views of the proximal portions and distal portions, respectively, of the introducer sheath of FIG. 18 and the thrombus collection device of FIG. 25 during another step of a percutaneous thrombus collection procedure.
Figure 34:
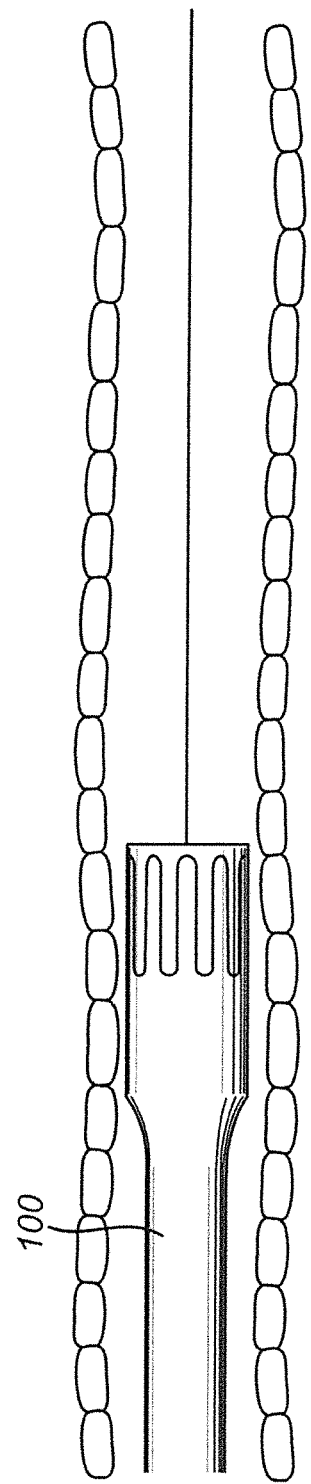

With continued reference to FIG. 32, the operator continues to pull back on the aspiration catheter 166 until all or substantially all of the thrombus 198 has been pulled into the sheath 100. The operator then continues to pull back on the aspiration catheter 166 in order to force the thrombus 198 out of the vasculature 154 through the sheath 100. The balloon 170 is withdrawn through the percutaneous access site and into the portion of the sheath 100 that is disposed outside the body. The compliant material of the sheath 100 is advantageously able to expand as the inflated balloon 170 passes so that the balloon 170 can push the pieces of thrombus 198 out of the body. The compliant sheath 100 then collapses as the elastic skin at the puncture site constricts, advantageously facilitating hemostasis. With reference to FIG. 33, the thrombus 198 and balloon 170 are eventually pulled through the proximal end 120 of the introducer sheath 100. The introducer sheath 100 may include a hinged proximal door 212 at the proximal end 120 that facilitates withdrawal of the inflated balloon 170.

Figure 35:
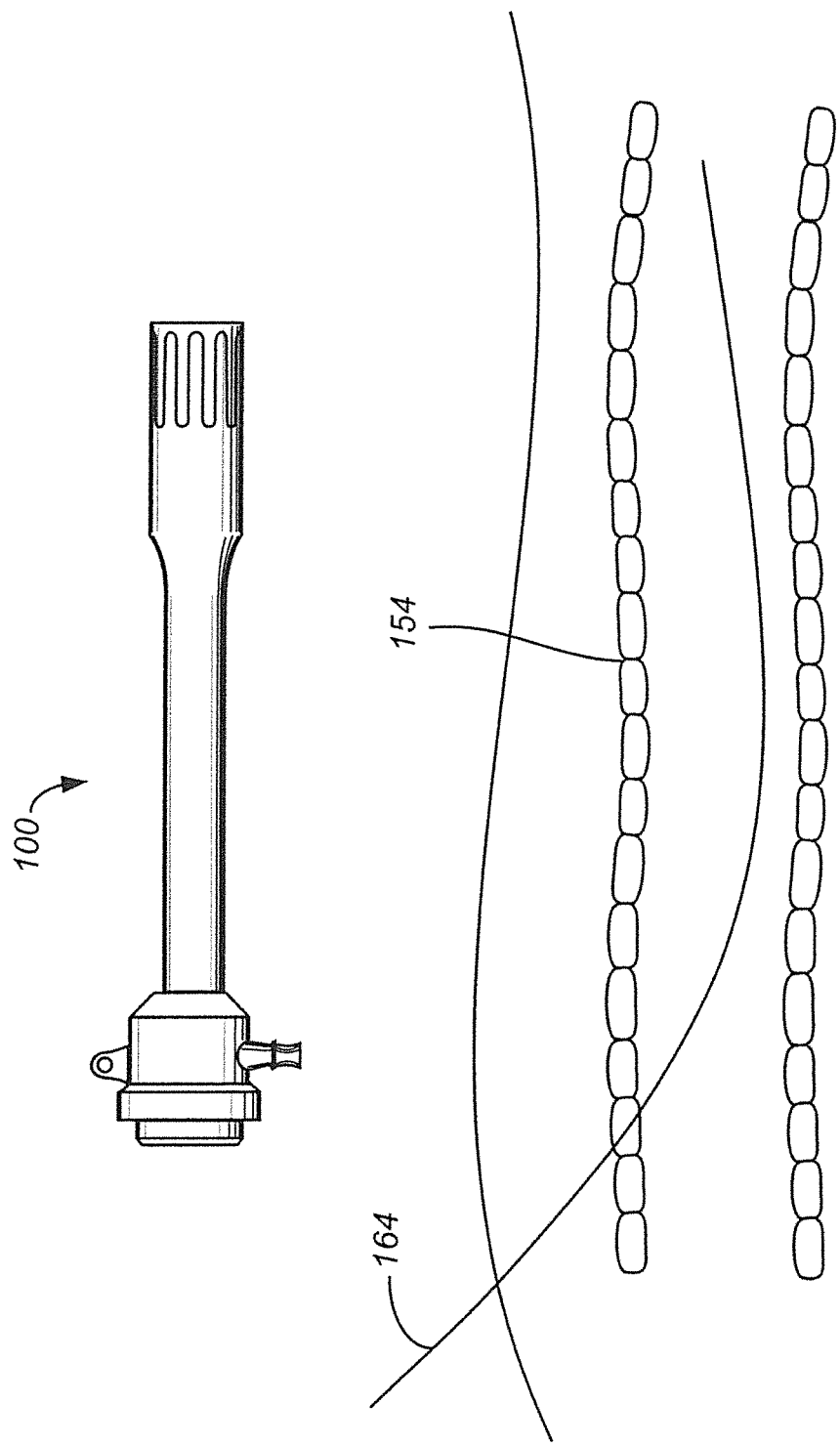
FIG. 35 is a side elevation view of the introducer sheath of FIG. 18 after withdrawal from a patient's vasculature during another step of a percutaneous thrombus collection procedure.

After the thrombus 198 has been removed from the vasculature 154 the introducer sheath 100 remains in the vasculature 154 through the percutaneous access site. The sheath 100 advantageously maintains a path into the vasculature 154 so that a guide wire 164 (FIG. 35) may be reinserted into the vasculature 154 as shown. It may be advantageous to reinsert a guide wire 164 so that the location of the removed thrombus 198 can be re-accessed. Repeat access may be desired so that the thrombus 198 removal procedure may be repeated or so that a stent may be placed, for example. After the guide wire 164 is reinserted, the introducer sheath 100 may be removed if desired, as shown in FIG. 35.

The aspiration catheter 166 illustrated in FIG. 25 includes three aspiration openings 182. The present aspiration catheters may include any number of aspiration openings 182. However, it has been found that three aspiration openings 182 achieve advantageous thrombus removal results. Further, providing more than one aspiration opening 182 advantageously maintains suction in the event that a first aspiration opening 182 becomes clogged. In the illustrated embodiments, each of the aspiration openings 182 on the catheter 166 has substantially the same diameter. However, in alternative embodiments the aspiration openings 182 could have varying diameters. For example, a diameter of the openings 182 may increase with increasing distance from the source of suction (the syringe 206 at the aspiration connector 180) in order to combat head losses across the openings 182.

Figure 36:
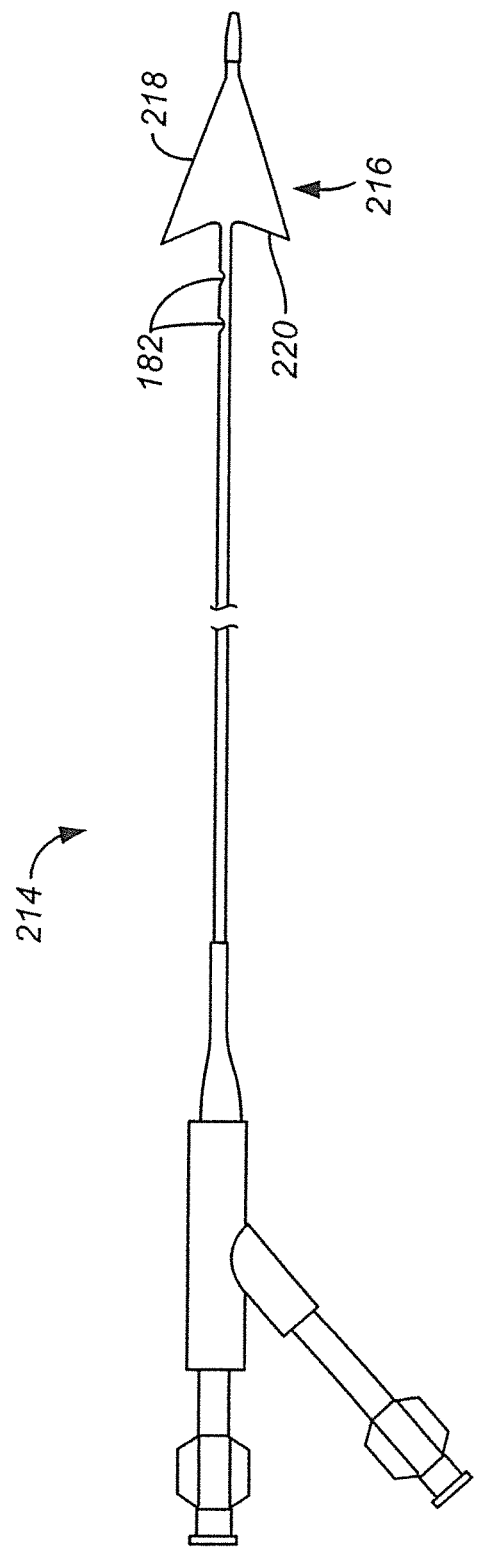
FIG. 36 is a side elevation view of another embodiment of the present thrombus collection device having aspiration ports.

FIG. 36 illustrates another embodiment of an aspiration catheter 214. The catheter 214 of FIG. 36 is similar to the catheter 166 of FIG. 25, except that it includes only two aspiration openings 182, and the distal balloon 216 has a different shape. The balloon 216 of FIG. 36 is shaped substantially as an arrowhead in profile. It includes a cone-shaped distal surface 218 and a proximal surface 220 shaped as an inverted cone. The inverted cone shape urges fluid to flow toward the centerline of the catheter 214 as the balloon 216 is pulled proximally. The flow direction carries thrombus particles toward the aspiration openings 182, where they are more likely to be sucked into the aspiration lumen 176. The balloon 216 thus increases the efficiency with which thrombus particles can be collected in the aspiration lumen 176.

As shown in FIGS. 27-35, the introducer sheath 100 of FIG. 18 may be used to introduce the aspiration catheter 166 of FIG. 25 into a patient's vasculature 154. However, both the introducer sheath 100 and the aspiration catheter 166 can be used in a wide variety of procedures other than a percutaneous thrombus collection procedure. For example, the introducer sheath 100 and the aspiration catheter 166 can be used in non-vascular locations such as the peritoneal cavity or other bodily cavities or hollow anatomical structures.

Further, both the introducer sheath 100 and the aspiration catheter 166 can be used with a wide variety of other apparatus. It should be understood that any of the apparatus described herein can be used separately, and/or in combination with any of the other apparatus described herein, and/or in combination with other apparatus not described herein. Several of these combinations are described below. It should be further understood that wherever the aspiration catheter 166 of FIG. 25 is described, the aspiration catheter 214 of FIG. 36 may be substituted therefore, wherever the sheath 100 of FIG. 18 is described, the sheath 20 of FIGS. 1-6 or the sheath 20' of FIG. 16 may be substituted therefore, and wherever the thrombus collection device 60 of FIGS. 7-10 is described, the thrombus collection device 60' of FIG. 17 may be substituted therefore.

Figure 37:
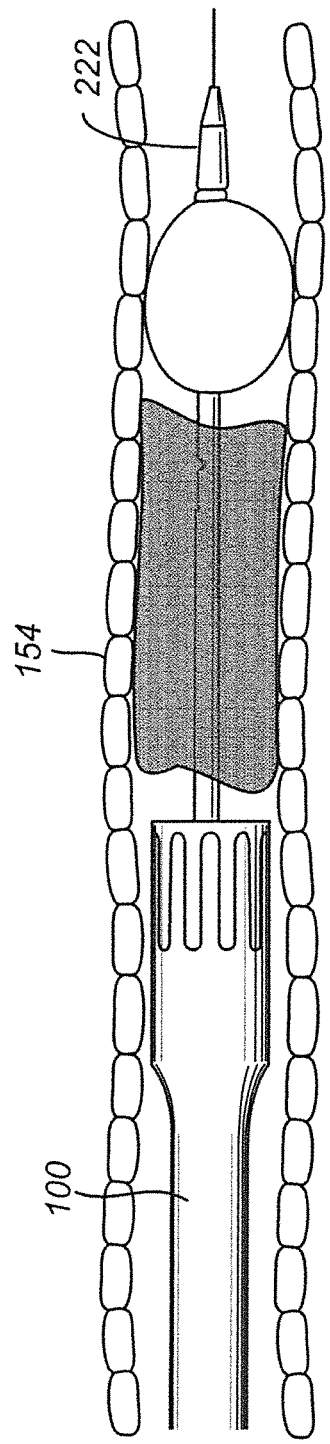
FIG. 37 is a side elevation view of the introducer sheath of FIG. 18 and a Fogarty balloon catheter disposed in a patient's vasculature during a percutaneous thrombus collection procedure.

With reference to FIG. 37, the introducer sheath 100 of FIG. 18 can be used to introduce a standard Fogarty balloon catheter 222 into the vasculature 154. Fogarty balloon catheters are well known, and will not be described in detail herein. The procedure for introducing the sheath 100 is as described above with respect to FIGS. 21-24, and the procedure for introducing the Fogarty catheter 222 is similar to the procedure described above with respect to FIGS. 27 and 28.

Figure 38:
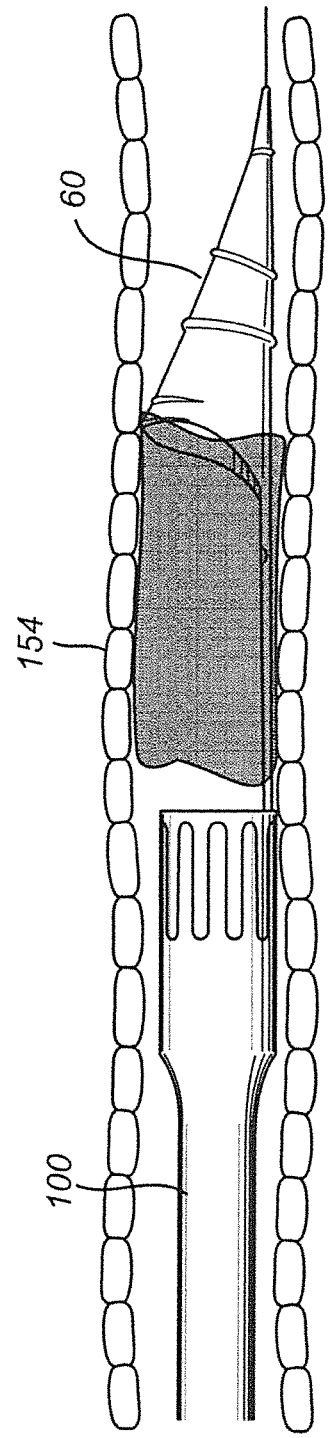
FIG. 38 is a side elevation view of the introducer sheath of FIG. 18 and the thrombus collection device of FIGS. 7-10 disposed in a patient's vasculature during a percutaneous thrombus collection procedure.

With reference to FIG. 38, the introducer sheath 100 of FIG. 18 can also be used to introduce the thrombus collection device 60 of FIGS. 7-10 into the vasculature 154. The procedure for introducing the sheath 100 is as described above with respect to FIGS. 21-24. The procedure for introducing the thrombus collection device 60 is described above with respect to FIGS. 11-15, except that the sheath 100 of FIG. 18 is substituted for the sheath 20 of FIGS. 1-6.

Figure 39:
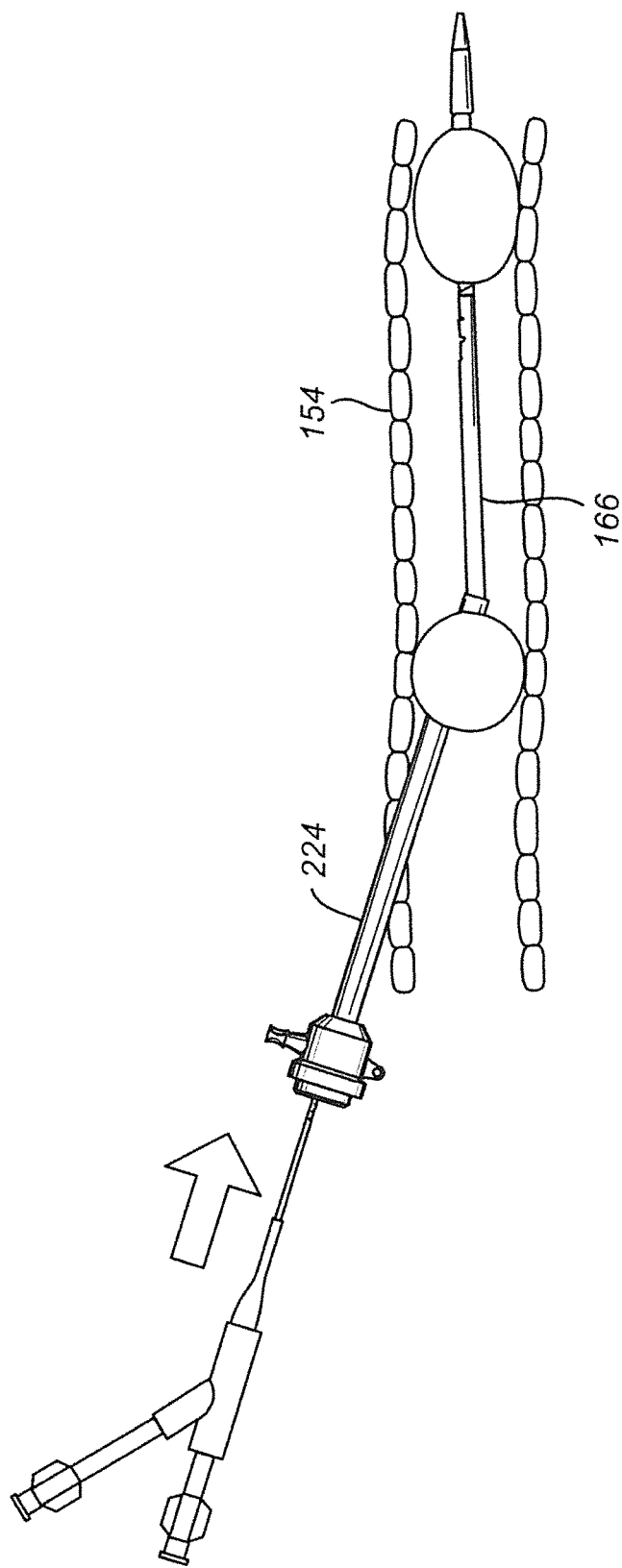
FIG. 39 is a side elevation view of a standard balloon catheter introducer sheath and the aspiration catheter of FIG. 25 disposed in a patient's vasculature during a percutaneous thrombus collection procedure.

With reference to FIG. 39, the aspiration catheter 166 of FIG. 25 can be introduced into the vasculature 154 through a standard balloon catheter introducer sheath 224. Balloon catheter introducer sheaths are well known, and will not be described in detail herein. The procedure for introducing the sheath 224 is similar to the procedure described above with respect to FIGS. 21-24. The procedure for introducing the aspiration catheter 166 is described above with respect to FIGS. 27 and 28, except that the balloon catheter introducer sheath 224 is substituted for the sheath 100 of FIG. 18.

While not illustrated herein, the introducer sheath 100 of FIG. 18 and the aspiration catheter 166 of FIG. 25 can also be used with other apparatus. For example, the sheath 20 of FIGS. 1-6 can be used to introduce the aspiration catheter 166 of FIG. 25 or the Fogarty balloon catheter 222 of FIG. 37. Further, the standard balloon catheter introducer sheath 224 of FIG. 39 can be used to introduce the thrombus collection device 60 of FIGS. 7-10.

As illustrated above, the present embodiments of the introducer sheath 100 and the aspiration catheter 166 offer numerous advantages. For example, with reference to the introducer sheath 100 of FIG. 18, the bell portion 104 expands upon deployment so that it contacts the interior walls of the vasculature 154 proximally of the thrombus 198 (FIGS. 24 and 28). When a balloon 170 is then placed distally of the thrombus 198 and inflated, the thrombus 198 is isolated between the bell portion 104 and the balloon 170. Since the bell portion 104 is open at its distal end 106, drawing back the balloon 170 sweeps the thrombus 198 into the open mouth of the bell portion 104. The removal process thus tends to reduce migration of thrombus 198, and to collect a greater amount of the thrombus 198 as opposed to procedures not including a sheath having a wide, open distal end.

The introducer sheath 100 of FIG. 18 is also advantageously compliant. It is thus able to expand to allow the withdrawal of thrombus 198 and an inflated catheter balloon 170. The sheath 100 thus enables a greater amount of thrombus 198 to be collected as compared to non-compliant sheaths 100. For example, clot burdens in arterio-venous fistulas (AVF) tend to be large, making them hard to remove percutaneously. The expandable compliant sheath 100 is well suited for removing these types of thrombus 198. Further, it is advantageous to remove the plug portion of a thrombus 198. The plug (not shown) is a relatively hard portion of thrombus 198 at the anastomosis where the vein is sewn to the artery. The harder plug tends not to compress as it is withdrawn percutaneously. The expandable compliant sheath 100 is thus well suited for removing the plug. The compliant nature of the sheath 100 facilitates removal of large thrombi 198 and plugs without need for macerating the thrombi and plugs or treating them with a thrombolytic agent before moving them through the sheath 100.

The expandable sheath 100 further enables devices of varying sizes to pass through it, so that various devices can be used during a single procedure without having to exchange the sheath 100 for a differently sized one. The compliant sheath 100 is also able to contract to maintain hemostasis at the percutaneous access site 156 after the catheter 166 has been withdrawn. The compliant sheath 100 further speeds hemostasis at the end of a procedure, because the skin and underlying tissue do not remain stretched for an extended period.

With reference to the aspiration catheter 166 of FIG. 25, the configuration of the catheter 166 advantageously provides push/pull inflation and aspiration. To inflate the balloon 170, the operator need only connect a syringe 200 filled with inflation liquid and push the plunger 204. To provide the suction force for thrombus aspiration, the operator need only connect an empty syringe 206, draw back and lock the plunger 208, then release the stopcock 202 while pulling on the catheter 166. This push/pull inflation and aspiration provides mechanical stability that contributes to lesser incidence of user error.

Both the introducer sheath 100 and the aspiration catheter 166 are also advantageously compatible with existing apparatus. As illustrated above, the introducer sheath 100 can be used to introduce a standard Fogarty balloon catheter 222, and the aspiration catheter 166 can be introduced with a standard balloon catheter introducer sheath 224. The introducer sheath 100 and the aspiration catheter 166 are thus easily adaptable to existing procedures that involve apparatus already familiar to those in the field.

What is claimed is:

1. A thrombus collection device comprising:
   a catheter including a sidewall defining a catheter opening;
   a casing at least partially co-extensive with at least a distal portion of the catheter along a longitudinal axis of the catheter; and
   an elongate wire at least partially co-extensive with at least the distal portion of the catheter, the elongate wire being slidable within a radial space between the casing and the catheter and configured to contract and expand the casing between a collapsed state and an expanded state in which the casing defines an opening to the radial space between the casing and the distal portion of the catheter that is longitudinally co-extensive with the casing,
   wherein the elongate wire extends out the catheter opening and along an outer surface of the catheter, and
   wherein the casing is configured to expand from the collapsed state to the expanded state in response to an application of a distally-directed force to the elongate wire that moves more of the elongate wire into the radial space between the casing and the catheter.

2. The thrombus collection device of claim 1, wherein the opening to the radial space and the radial space between the casing and the distal portion of the catheter are configured to receive a thrombus, wherein the wire is configured to maintain the casing in the expanded state when the wire is held stationary with respect to the catheter, and maintain the casing in the expanded state when the thrombus collection device is drawn proximally through the thrombus, in response to an application of a proximally-directed force to the catheter, such that the thrombus is collected within the radial space between the casing and the distal portion of the catheter.

3. The thrombus collection device of claim 1, wherein the wire is freely slidable within the radial space between the casing and the distal portion of the catheter, and wherein the wire is configured to slide within the radial space between the casing and the distal portion of the catheter in response to the application of the distally-directed force to the wire.

4. The thrombus collection device of claim 1, wherein the casing and the wire are configured such that application of the distally-directed force to the wire increases a size of the opening to the radial space.

5. The thrombus collection device of claim 1, wherein a distal end of the wire is secured to the catheter.

6. The thrombus collection device of claim 1, wherein a distal end of the wire is movable relative to the casing and the catheter.

7. The thrombus collection device of claim 1, wherein the casing has a tubular shape.

8. The thrombus collection device of claim 1, wherein a proximal end of the casing defines the opening to the radial space and the casing defines a closed distal end when the casing is in the expanded state.

9. The thrombus collection device of claim 1, wherein the casing is elastomeric.

10. The thrombus collection device of claim 1, wherein the casing is configured to conform to vasculature of a patient such that a proximal end of the casing is configured to conform to an interior diameter of the vasculature when the casing is in the expanded state.

11. The thrombus collection device of claim 1, wherein the catheter defines a lumen, wherein the wire is configured to extend through the lumen from a proximal portion of the catheter to the catheter opening in the sidewall of the catheter and exit the lumen via the catheter opening, and wherein the wire extends exteriorly of the catheter at least partially along the distal portion of the catheter between the casing and the catheter.

12. The thrombus collection device of claim 1, wherein the wire forms a helix including a plurality of coils that wrap around the distal portion of the catheter.

13. The thrombus collection device of claim 12, wherein the application of the distally-directed force to the elongate wire comprises an application of a compressive force to the wire, and wherein the wire is configured to move distally along the distal portion of the catheter such that the coils of the helix tighten and form increasingly larger diameters to expand the casing in response to the application of the compressive force.

14. The thrombus collection device of claim 12, wherein the coils of the helix are configured to relax and form increasingly smaller diameters in response to an application of a tensile force to the wire.

15. The thrombus collection device of claim 12, wherein there are no pleats in the casing between adjacent coils of the plurality of coils when the casing is in the expanded state.

16. A system comprising:
the thrombus collection device of claim 1; and
an introducer sheath configured to be introduced into vasculature of a patient, wherein the thrombus collection device is configured to be introduced into the vasculature through the introducer sheath, and wherein the casing comprises a first casing and the wire comprises a first wire, the introducer sheath comprising:
a second casing comprising an inner layer and an outer layer, the inner layer defining a lumen configured to receive the thrombus collection device; and
a second wire at least partially co-extensive with at least a distal portion of the second casing along a longitudinal axis of the second casing, the second wire being slidable within a radial space between the inner layer and the outer layer and configured to contract and expand the second casing between a collapsed state and an expanded state in which the lumen is sized to receive the thrombus collection device,
wherein the second casing is configured to expand from the collapsed state to the expanded state in response to an application of a distally-directed force to the second wire that moves more of the second wire into the radial space between the inner layer and the outer layer.

17. The system of claim 16, wherein the distal portion of the second casing defines a proximally-tapering shape when the second casing is in the expanded state.

18. The system of claim 16, wherein the application of the distally-directed force to the second wire increases a size of the lumen.

19. The thrombus collection device of claim 1, wherein, while in the expanded state, the casing is oriented radially asymmetrically relative to the longitudinal axis of the catheter.

20. A thrombus collection device comprising:
a catheter;
a casing at least partially co-extensive with at least a distal portion of the catheter along a longitudinal axis of the catheter; and
an elongate wire at least partially co-extensive with at least the distal portion of the catheter, the elongate wire being slidable within a radial space between the casing and the catheter and configured to contract and expand the casing between a collapsed state and an expanded state in which the casing defines an opening to the radial space between the casing and the distal portion of the catheter that is longitudinally co-extensive with the casing,
wherein the elongate wire extends exteriorly of the catheter from a proximal end of the elongate wire to a distal end of the elongate wire, and
wherein the casing is configured to expand from the collapsed state to the expanded state in response to an application of a distally-directed force to the elongate wire that moves more of the elongate wire into the radial space between the casing and the catheter.

21. A thrombus collection device comprising:
a catheter;
a casing at least partially co-extensive with at least a distal portion of the catheter; and
an elongate wire that forms a helix comprising a plurality of coils that wrap around at least the distal portion of the catheter, the wire being slidable within a space between the casing and the catheter and configured to contract and expand the casing between a collapsed state and an expanded state in which the casing defines an opening to the space between the casing and the catheter,
wherein the casing is configured to expand from the collapsed state to the expanded state in response to an application of a distally-directed compressive force to the elongate wire, and wherein the coils of the helix tighten and form increasingly larger diameters to expand the casing in response to the application of the compressive force to the elongate wire.

22. The thrombus collection device of claim 21, wherein the application of the compressive force to the wire moves more of the wire into the space between the casing and the catheter.

23. The thrombus collection device of claim 22, wherein the elongate wire is configured to move distally along the distal portion of the catheter to tighten the coils of the helix and form the increasingly larger diameters to expand the casing in response to the application of the compressive force to the elongate wire.

24. The thrombus collection device of claim 21, wherein the wire is freely slidable within the space between the casing and the catheter, and wherein the wire is configured to slide within the space between the casing and the catheter in response to the application of the distally-directed compressive force to the wire.

25. The thrombus collection device of claim 21, wherein the coils of the helix are configured to relax and form increasingly smaller diameters in response to an application of a tensile force to the wire.

26. The thrombus collection device of claim 21, wherein there are no pleats in the casing between adjacent coils of the plurality of coils when the casing is in the expanded state.

* * * * *